US012605316B2

(12) United States Patent
O'Neil et al.

(10) Patent No.: US 12,605,316 B2
(45) Date of Patent: *Apr. 21, 2026

(54) ALKENONE-BASED FORMULATIONS FOR TOPICAL APPLICATIONS

(71) Applicants: Woods Hole Oceanographic Institution, Woods Hole, MA (US); Western Washington University, Bellingham, WA (US)

(72) Inventors: Gregory W. O'Neil, Bellingham, WA (US); Christopher M. Reddy, Woods Hole, MA (US)

(73) Assignees: Woods Hole Oceanographic Institution, Woods Hole, MA (US); Western Washington University, Bellingham, WA (US)

(*) Notice: Subject to any disclaimer, the term of this patent is extended or adjusted under 35 U.S.C. 154(b) by 101 days.

This patent is subject to a terminal disclaimer.

(21) Appl. No.: 18/386,498

(22) Filed: Nov. 2, 2023

(65) Prior Publication Data

US 2024/0122828 A1 Apr. 18, 2024

Related U.S. Application Data

(63) Continuation of application No. 17/397,256, filed on Aug. 9, 2021, now Pat. No. 11,839,675, which is a continuation of application No. 15/776,401, filed as application No. PCT/US2016/062307 on Nov. 16, 2016, now Pat. No. 11,110,043.

(60) Provisional application No. 62/255,961, filed on Nov. 16, 2015.

(51) Int. Cl.

| | |
|---|---|
| ***A61K 8/33*** | (2006.01) |
| ***A61K 8/35*** | (2006.01) |
| ***A61K 8/36*** | (2006.01) |
| ***A61K 8/37*** | (2006.01) |
| ***A61K 8/41*** | (2006.01) |
| ***A61K 8/44*** | (2006.01) |
| ***A61K 8/55*** | (2006.01) |
| ***A61K 8/9711*** | (2017.01) |
| ***A61K 8/9717*** | (2017.01) |
| ***A61K 8/9728*** | (2017.01) |
| ***A61K 8/9741*** | (2017.01) |
| ***A61K 8/9761*** | (2017.01) |
| ***A61K 8/9767*** | (2017.01) |
| ***A61K 8/9771*** | (2017.01) |
| ***A61K 8/9789*** | (2017.01) |
| ***A61K 8/9794*** | (2017.01) |
| ***A61Q 5/00*** | (2006.01) |
| ***A61Q 19/00*** | (2006.01) |

(52) U.S. Cl.

CPC .................. *A61K 8/33* (2013.01); *A61K 8/35* (2013.01); *A61K 8/361* (2013.01); *A61K 8/37* (2013.01); *A61K 8/416* (2013.01); *A61K 8/442* (2013.01); *A61K 8/55* (2013.01); *A61K 8/9711* (2017.08); *A61K 8/9717* (2017.08); *A61K 8/9728* (2017.08); *A61K 8/9741* (2017.08); *A61K 8/9761* (2017.08); *A61K 8/9767* (2017.08); *A61K 8/9771* (2017.08); *A61K 8/9789* (2017.08); *A61K 8/9794* (2017.08); *A61Q 5/00* (2013.01); *A61Q 19/00* (2013.01); *A61K 2800/10* (2013.01); *A61K 2800/43* (2013.01); *A61K 2800/48* (2013.01); *A61K 2800/49* (2013.01); *A61K 2800/51* (2013.01); *A61K 2800/52* (2013.01); *A61K 2800/522* (2013.01); *A61K 2800/524* (2013.01)

(58) Field of Classification Search

None

See application file for complete search history.

(56) References Cited

U.S. PATENT DOCUMENTS

2010/0080761 A1* 4/2010 Herrmann ................ A61Q 7/00 424/59

OTHER PUBLICATIONS

Marlowe, I.T., et al. "Long chain (n-C37-C39) alkenones in the Prymnesiophyceae. Distribution of alkenones and other lipids and their taxonomic significance." British Phycological Journal 19.3 (1984): 203-216. (Year: 1984).*

O'Neil, Gregory W., et al. "Beyond fatty acid methyl esters: Expanding the renewable carbon profile with alkenones from *Isochrysis* sp." Energy & fuels 26.4 (2012): 2434-2441 and S1-S3. (Year: 2012).*

* cited by examiner

*Primary Examiner* — Bethany P Barham

*Assistant Examiner* — Peter Anthopolos

(74) *Attorney, Agent, or Firm* — CHRISTENSEN O'CONNOR JOHNSON KINDNESS PLLC

(57) ABSTRACT

The use of long-chain alkenones to impart desired characteristics in personal care compositions for topical applications is described. The preparation of mixtures long-chain alkenones and synthetic derivatives thereof is presented. Examples of compositions include abrasive soaps, with alkenones serving as natural exfoliating agents. Alkenones and their derivatives can serve as emollients, occlusive agents, stabilizing agents, binding agents, thickening agents, surfactants, and antimicrobials.

7 Claims, 8 Drawing Sheets

(a) 38:3 ethyl alkenone (b) 18:2 linoleic acid (a) 16:0 stearic acid (b) 18:1 oleic acid myristic acid 1-tetradecanol myristyl myristate lipophilic hydrophilic glyceryl monostearate (GMS)

(Part A)

(Part B)

alkenone-based emulsifier GMA

ALKENONE-BASED FORMULATIONS FOR TOPICAL APPLICATIONS

CROSS-REFERENCE TO RELATED APPLICATION

This application is a continuation of U.S. Non-Provisional Ser. No. 17/397,256 filed Aug. 9, 2021, now allowed, which is a continuation of U.S. Non-Provisional Ser. No. 15/776,401 filed as application No. PCT/US16/62307 on Nov. 16, 2016, now U.S. Pat. No. 11,110,043, which claims the benefit of U.S. Provisional Patent Application No. 62/255,961, filed Nov. 16, 2015, the disclosure of the above referenced applications which are hereby incorporated by reference in their entireties.

BACKGROUND

Many consumer products rely on petroleum-derived compounds to provide the necessary properties for their intended use. However, with growing health and environmental concerns about the use of petrochemicals, there is a need for alternative compounds from renewable and sustainable sources. For example, plastic-exfoliating beads have been recently banned in some states. See, e.g., Abrams, R., "Fighting Pollution from Microbeads Used in Soaps and Creams," *New York Times*, May 22, 2015.

Abrasives are common to a variety of cleansers (e.g., body washes, facial cleansers, etc.) because they can produce a softer skin feel, and are typically made from polymers such as polyethylene, a petroleum-derived material. Widespread daily use of these products has produced an enormous accumulation and persistence of polymeric abrasives in the marine and fresh water environment whose impact, to even human health, is only recently becoming appreciated. See, e.g., Yang, D. et al., "Microplastic Pollution in Table Salts from China," *Environ. Sci. Tech.* 2015, 49, pp 13622-13627, DOI: 10.1021/acs.est.5b03163. Replacing microplastics of this type while maintaining quality is, however, challenging, as other natural or biodegradable ingredients such as ground fruit pits and nut shells fail to match the smoothness of polyethylene beads, resulting in increased skin damage.

Algae are highly prized as rich and diverse sources of various renewable high-value chemicals. One example is within the omega-3 polyunsaturated fatty acid ("PUFA") market. In 2012, the global market for microalgae docosahexaenoic acid (DHA), an essential omega-3, a PUFA that has been tied to brain health, was estimated to be $350 million and about 4,600 metric tons. See, e.g., Shanahan, C., "The global algae oil omega-3 market in 2014," *Algae Industry Magazine.com*, May 18, 2014. Infant formula applications represented nearly half of the microalgae-based DHA market, followed by dietary supplements and food/beverages.

Benefits of algae-derived chemicals include the ability of some algae to grow in brackish water, salt water, or wastewater, or on otherwise non-arable land, thus not competing for water or land resources. As photosynthetic organisms, algae also fix $CO_2$, thereby decreasing atmospheric concentrations of this problematic greenhouse gas when compared to burning petroleum fuels. Additionally, unlike traditional agricultural crops, the use of algae to make non-food products would not affect food supplies and prices.

Accordingly, there is a need for replacement of petroleum-derived compounds with compounds from renewable sources. The present disclosure seeks to fulfill these needs and provides related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides, inter alfa, a personal care composition, including:

a compound of Formula (I):

(I)

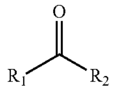

wherein $R_1$ is methyl or ethyl; and $R_2$ is a $C_{30-45}$ alkenyl having at least one trans double carbon-carbon bond, or $R_2$ is a $C_{30-45}$ alkyl;

provided that the compound of Formula (I) is not

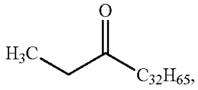,
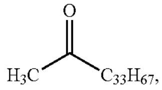,
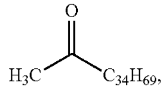, or
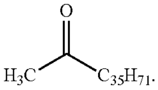.

In another aspect, the present disclosure provides, inter alfa, a personal care composition, including:

at least one compound of Formula (II), Formula (III), or Formula (IV):

(II)

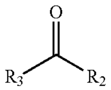

wherein $R_3$ is selected from —OH, —$O(CH_2CH_2)_nOSO_3$—, and —$O(CH_2)(CHOH)(CHOH)$, wherein n is an integer of from 1 to 200, and $R_2$ is a $C_{30-45}$ alkenyl having at least one trans double carbon-carbon bond, or $R_2$ is a $C_{30-45}$ alkyl;

(III)

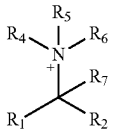

wherein $R_1$ is methyl or ethyl;

$R_2$ is a $C_{30-45}$ alkenyl having at least one trans double carbon-carbon bond, or $R_2$ is a $C_{30-45}$ alkyl;

$R_4$, $R_5$, and $R_6$ are each independently selected from H, $C_{1-6}$ alkyl, $C_{1-6}$ haloalkyl, and halo; and $R_7$ is selected from H and $—CO_2—$;

(IV)

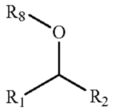

wherein $R_1$ is methyl or ethyl;

$R_2$ is a $C_{30-45}$ alkenyl having at least one trans double carbon-carbon bond, or $R_2$ is a $C_{30-45}$ alkyl;

$R_8$ is selected from $—SO_3—$, $—PO_2—OR_9$, and $—CONHR_{10}$, wherein $R_9$ is $—CH_2CH_2N^+R_{11}R_{12}R_{13}$, wherein $R_{11}$, $R_{12}$, and $R_{13}$ are each independently selected from H, $C_{1-6}$ alkyl, $C_{1-6}$ haloalkyl, and halo, and $R_{10}$ is $—(CH_2)_mSO_3—$, $—(CH_2)_mN^+R_{14}R_{15}CH_2CO_2—$, $—(CH_2)_mN^+R_{16}R_{17}R_{18}$, wherein m is an integer of from 1 to 10; $R_{14}$, $R_{15}$, $R_{16}$, $R_{17}$, and $R_{18}$ are each independently selected from H, $C_{1-6}$ alkyl, $C_{1-6}$ haloalkyl, and halo.

In yet another aspect, the present disclosure provides, inter alia, a composition, including:

at least one polyunsaturated long-chain alkenone derivative of Formula (V):

(V)

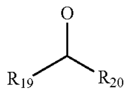

wherein $R_{19}$ is a polar head group, and $R_{20}$ is a $C_{30-45}$ alkenyl having at least one trans double carbon-carbon bond, or $R_{20}$ is a $C_{30-45}$ alkyl.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings.

DETAILED DESCRIPTION

The present disclosure describes the use of alkenones and alkenone-derived compounds in eco-friendly personal care products. The disclosure also provides methods for the manipulation of algal extracts to provide various combinations of alkenones along with other naturally occurring compounds such as oils (e.g., fatty acids and derivatives) and pigments (e.g., carotenoids and chlorophylls). In other aspects, alkenones and/or synthetic alkenone derivatives are used to provide personal care compositions with desirable properties ranging from mild skin cleansers to cosmetics.

Figure 1A:
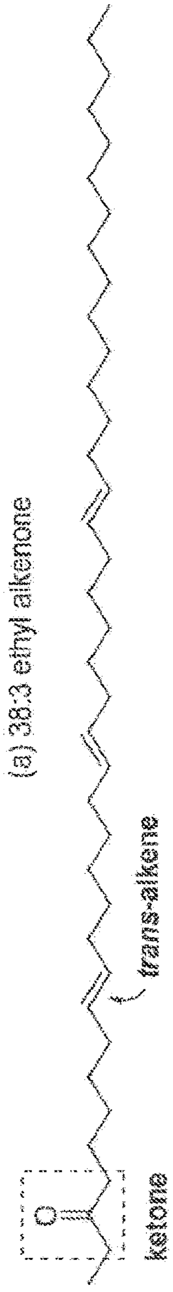
FIG. 1A shows the structure of an embodiment of an alkenone produced by *Isochyrsis* sp. As used herein, the nomenclature for alkenones corresponds to the total number of carbons:number of double bonds.
Figure 1B:
FIG. 1B shows the structure of an embodiment of a fatty acid, specifically linoleic acid. The alkenone nomenclature corresponds to the total number of carbons:number of double bonds.

Referring to FIG. 1A, alkenones of the present disclosure have structures that are characterized by very long hydrocarbon chains (e.g., 36 to 40 carbons; approximately twice as long as typical fatty acids), giving these compounds high melting points (~70° C.) and making them white waxy solids at room temperature. They contain trans-double carbon-carbon bonds—as opposed to less stable cis-configured methylene interrupted double bonds present in fatty acids (FIG. 1B)—and are a methyl or ethyl ketone.

The alkenones of the present disclosure can be biologically synthesized by the marine microalgae *Isochrysis*. *Isochrysis* provides many advantages. For example, *Isochrysis* is one of only a few species of algae with a history of industrial production and is one of only a select number of algae that biosynthesize a unique suite of lipids known as polyunsaturated long-chain alkenones (PULCA). Long-chain unsaturated methyl and ethyl ketones (alkenones) are part of a group of unusual compounds including related alkenes and alkenoates collectively referred to as PULCAs. In addition to *Isochrysis*, alkenones can be biosynthesized by other haptophyte microalgae, including the ocean coccolithophorid *Emiliania huxleyi* and the closely related species *Gephyrocapsa oceanica*. Often these neutral lipids are more abundant than triacylglycerols, especially in the stationary-phase of growth curves. It is believed that PULCAs reside in cytoplasmic lipid bodies for energy storage. See, e.g., Eltgroth, M. L., et al., "Production and cellular localization of long-chain neutral lipids in the haptophyte algae *Isochrysis galbana* and *Emiliania huxleyi*," *J. Phycol.* 2005, 41, 1000-1009.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the disclosure, which are, for clarity, described in the context of separate embodiments, can also be provided in combination in a single embodiment.

Conversely, various features of the disclosure which are, for brevity, described in the context of a single embodiment, can also be provided separately or in any suitable sub comb inati on.

As used herein, the term "substituted" or "substitution" refers to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, the nomenclature for alkenones corresponds to the total number of carbons:number of double bonds. A methyl or ethyl substituent on the alkenone is indicated as Me or Et, respectively.

As used herein, the term "alkyl" refers to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 50, from 1 to about 45, from 1 to about 40, from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "aryl" refers to monocyclic or polycyclic (e.g., having 2, 3, or 4 fused rings) aromatic hydrocarbons such as, for example, phenyl, naphthyl, anthracenyl, phenanthrenyl, indanyl, and indenyl. In some embodiments, aryl groups have from 6 to about 20 carbon atoms.

As used herein, "arylene" refers to a linking aryl group.

As used herein, the term "halo" or "halogen" includes fluoro, chloro, bromo, and iodo.

As used herein, the term "alkylene" refers to a linking alkyl group.

As used herein, "alkenyl" refers to an alkyl group having one or more double carbon-carbon bonds. The double bond can be trans or cis, where when the two alkyl groups are on the same side of the C═C, the double bond is referred to as cis; and when the alkyl groups are oriented in opposing directions, the double is referred to as trans. The alkenyl group can be linear or branched. Example alkenyl groups include ethenyl, propenyl, and the like. An alkenyl group can contain from 2 to about 50, from 2 to about 45, from 2 to about 40, from 2 to about 35, from 2 to about 30, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "alkynyl" refers to an alkyl group having one or more triple carbon-carbon bonds. The alkynyl group can be linear or branched. Example alkynyl groups include ethynyl, propynyl, and the like. An alkynyl group can contain from 2 to about 50, from 2 to about 45, from 2 to about 40, from 2 to about 35, from 2 to about 30, from 2 to about 24, from 2 to about 20, from 2 to about 10, from 2 to about 8, from 2 to about 6, or from 2 to about 4 carbon atoms.

As used herein, "alkynylene" refers to a linking alkynyl group.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "haloalkenyl" refers to an alkenyl group having one or more halogen substituents.

As used herein, "haloalkynyl" refers to an alkynyl group having one or more halogen substituents.

As used herein, "haloalkoxy" refers to an —O-(haloalkyl) group.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbomyl, norpinyl, norcamyl, adamantyl, and the like.

As used herein, "cycloalkylene" refers to a linking cycloalkyl group.

As used herein, "heteroalkyl" refers to an alkyl group having at least one heteroatom such as sulfur, oxygen, or nitrogen.

As used herein, "heteroalkylene" refers to a linking heteroalkyl group.

As used herein, a "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, the term "fatty acid" refers to a molecule having a carboxylic acid with a long aliphatic chain, which is either saturated or unsaturated.

As used herein, the term "fatty acid ester" refers to a long aliphatic chain (saturated or unsaturated) having a —C(O)O— moiety at an end of the chain.

As used herein, the term "fatty acid amide" refers to a long aliphatic chain (saturated or unsaturated) having a —C(O)NR— moiety at an end of the chain.

As used herein, the term "constitutional unit" of a polymer refers to an atom or group of atoms in a polymer, comprising a part of the chain together with its pendant atoms or groups of atoms, if any. The constitutional unit can refer to a repeat unit. The constitutional unit can also refer to an end group on a polymer chain. For example, the constitutional unit of polyethylene glycol can be $—CH_2CH_2O—$ corresponding to a repeat unit, or $—CH_2CH_2OH$ corresponding to an end group.

As used herein, the term "repeat unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

As used herein, the term "terminus" of a polymer refers to a constitutional unit of the polymer that is positioned at the end of a polymer backbone.

As used herein, the term "biodegradable" refers to a process that degrades a material via hydrolysis and/or a catalytic degradation process, such as enzyme-mediated hydrolysis and/or oxidation. For example, polymer side chains can be cleaved from the polymer backbone via either hydrolysis or a catalytic process (e.g., enzyme-mediated hydrolysis and/or oxidation).

As used herein, "biocompatible" refers to a property of a molecule characterized by it, or its in vivo degradation products, being not, or at least minimally and/or reparably, injurious to living tissue; and/or not, or at least minimally and controllably, causing an immunological reaction in living tissue. As used herein, "physiologically acceptable" is interchangeable with biocompatible.

As used herein, the term "hydrophobic" refers to a moiety that is not attracted to water with significant apolar surface area at physiological pH and/or salt conditions. This phase separation can be observed via a combination of dynamic light scattering and aqueous NMR measurements. Hydrophobic constitutional units tend to be non-polar in aqueous conditions. Examples of hydrophobic moieties include alkyl groups, aryl groups, etc.

As used herein, the term "hydrophilic" refers to a moiety that is attracted to and tends to be dissolved by water. The hydrophilic moiety is miscible with an aqueous phase. Hydrophilic constitutional units can be polar and/or ionizable in aqueous conditions. Hydrophilic constitutional units can be ionizable under aqueous conditions and/or contain polar functional groups such as amides, hydroxyl groups, or ethylene glycol residues. Examples of hydrophilic moieties include carboxylic acid groups, amino groups, hydroxyl groups, etc.

As used herein, the term "cationic" refers to a moiety that is positively charged, or ionizable to a positively charged moiety under physiological conditions. Examples of cationic moieties include, for example, amino, ammonium, pyridinium, imino, sulfonium, quaternary phosphonium groups, etc.

As used herein, the term "anionic" refers to a functional group that is negatively charged, or ionizable to a negatively charged moiety under physiological conditions. Examples of anionic groups include carboxylate, sulfate, sulfonate, phosphate, etc.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Personal Care Compositions

As discussed above, in one aspect, the present disclosure features a personal care composition including one or more alkenones or alkenone-derived compounds, such as a compound of Formula (I):

(I)

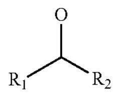

wherein $R_1$ is methyl or ethyl; and $R_2$ is a $C_{30-45}$ alkenyl having at least one trans double carbon-carbon bond, or $R_2$ is a $C_{30-45}$ alkyl;

provided that the compound of Formula (I) is not

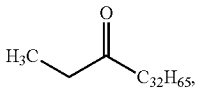

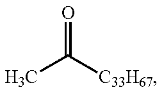

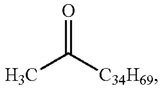

or

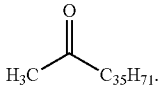

In another aspect, the personal care composition includes a compound of Formula (I):

(I)

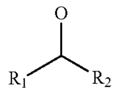

wherein $R_1$ is methyl or ethyl; and $R_2$ is a $C_{30-45}$ alkenyl having at least one trans double carbon-carbon bond.

In yet another aspect, the personal care composition includes a compound of Formula (I):

(I)

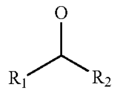

wherein $R_1$ is methyl or ethyl; and $R_2$ is a $C_{32-45}$ alkyl;

provided that the compound of Formula (I) is not

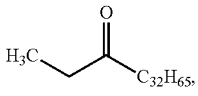

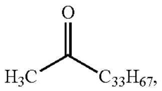

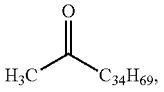

or

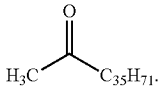

In a further aspect, the personal care composition includes a compound of Formula (I):

(I)

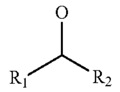

wherein $R_1$ is methyl or ethyl; and $R_2$ is a $C_{33-45}$ alkyl;

provided that the compound of Formula (I) is not

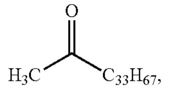

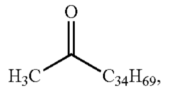

or

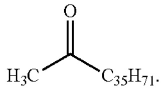

In yet another aspect, the present disclosure features a personal care composition, including at least one compound of Formula (II), Formula (III), or Formula (IV):

(II)

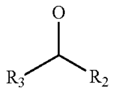

wherein $R_3$ is selected from —OH, —$O(CH_2CH_2)_nOSO_3$—, and —$O(CH_2)(CHOH)(CHOH)$, wherein n is an integer of from 1 to 200, and $R_2$ is a $C_{30-45}$ alkenyl having at least one trans double carbon-carbon bond, or $R_2$ is a $C_{30-45}$ alkyl;

(III)

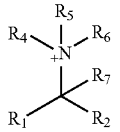

wherein $R_1$ is methyl or ethyl;

$R_2$ is a $C_{30-45}$ alkenyl having at least one trans double carbon-carbon bond, or $R_2$ is a $C_{30-45}$ alkyl;

$R_4$, $R_5$, and $R_6$ are each independently selected from H, $C_{1-6}$ alkyl, $C_{1-6}$ haloalkyl, and halo; and $R_7$ is selected from H and —$CO_2$—;

(IV)

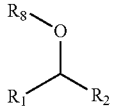

wherein $R_1$ is methyl or ethyl;

$R_2$ is a $C_{30-45}$ alkenyl having at least one trans double carbon-carbon bond, or $R_2$ is a $C_{30-45}$ alkyl;

$R_8$ is selected from —$SO_3$—, $PO_2$—$OR_9$, and —$CONHR_{10}$, wherein $R_9$ is —$CH_2CH_2N^+R_{11}R_{12}R_{13}$, wherein $R_{11}$, $R_{12}$, and $R_{13}$ are each independently selected from H, $C_{1-6}$ alkyl, $C_{1-6}$ haloalkyl, and halo, and $R_{10}$ is $(CH_2)_mSO_3$—, $(CH_2)_mN^+R_{14}R_{15}CH_2CO_2$—, $(CH_2)_mN^+R_{16}R_{17}R_{18}$, wherein m is an integer of from 1 to 10; $R_{14}$, $R_{15}$, $R_{16}$, $R_{17}$, and $R_{18}$ are each independently selected from H, $C_{1-6}$ alkyl, $C_{1-6}$ haloalkyl, and halo.

In yet another aspect, the present disclosure features a personal care composition, including at least one compound of Formula (II), Formula (III), or Formula (IV):

(II)

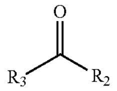

wherein $R_3$ is selected from —OH, —$O(CH_2CH_2)_nOSO_3$—, and —$O(CH_2)(CHOH)(CHOH)$, wherein n is an integer of from 1 to 200, and $R_2$ is a $C_{30-45}$ alkenyl having at least one trans double carbon-carbon bond, or $R_2$ is a $C_{36-45}$ alkyl;

(III)

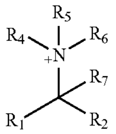

wherein $R_1$ is methyl or ethyl;

$R_2$ is a $C_{30-45}$ alkenyl having at least one trans double carbon-carbon bond, or $R_2$ is a $C_{36-45}$ alkyl;

$R_4$, $R_5$, and $R_6$ are each independently selected from H, $C_{1-6}$ alkyl, $C_{1-6}$ haloalkyl, and halo; and $R_7$ is selected from H and —$CO_2$—;

(IV)

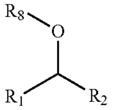

wherein $R_1$ is methyl or ethyl;

$R_2$ is a $C_{30-45}$ alkenyl having at least one trans double carbon-carbon bond, or $R_2$ is a $C_{36-45}$ alkyl;

$R_8$ is selected from —$SO_3$—, —$PO_2$—$OR_9$, and —$CONHR_{10}$, wherein $R_9$ is —$CH_2CH_2N^+R_{11}R_{12}R_{13}$, wherein $R_{11}$, $R_{12}$, and $R_{13}$ are each independently selected from H, $C_{1-6}$ alkyl, $C_{1-6}$ haloalkyl, and halo, and $R_{10}$ is —$(CH_2)_mSO_3$—, —$(CH_2)_mN^+R_{14}R_{15}CH_2CO_2$—, —$(CH_2)_mN^+R_{16}R_{17}R_{18}$, wherein m is an integer of from 1 to 10; $R_{14}$, $R_{15}$, $R_{16}$, $R_{17}$, and $R_{18}$ are each independently selected from H, $C_{1-6}$ alkyl, $C_{1-6}$ haloalkyl, and halo.

In yet another aspect, the present disclosure features a composition including at least one compound of Formula (V):

(V)

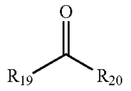

wherein $R_{19}$ is a polar head group, and $R_{20}$ is a $C_{30-45}$ alkenyl having at least one trans double carbon-carbon bond, or $R_{20}$ is a $C_{30-45}$ alkyl.

Aspects of the compositions above can have one or more of the following features.

In some embodiments, $R_2$ is an alkenyl having at least 34 carbons and at least one trans double carbon-carbon bond.

In some embodiments, $R_2$ is an alkenyl having at least 35 carbons and at least one trans double carbon-carbon bond.

In some embodiments, $R_2$ is a $C_{34-45}$ alkenyl having at least one trans double carbon-carbon bond.

In some embodiments, $R_2$ is a $C_{35-45}$ alkenyl having at least one trans double carbon-carbon bond.

In some embodiments, $R_2$ is a $C_{36-45}$ alkenyl having at least one trans double carbon-carbon bond.

In some embodiments, $R_2$ is a $C_{34-40}$ alkenyl having at least one trans double carbon-carbon bond.

In some embodiments, $R_2$ is a $C_{35-40}$ alkenyl having at least one trans double carbon-carbon bond.

In some embodiments, $R_2$ is a $C_{36-40}$ alkenyl having at least one trans double carbon-carbon bond.

In some embodiments, $R_2$ has 2 to 4 trans double carbon-carbon bonds.

In some embodiments, $R_2$ has 2 trans double carbon-carbon bonds.

In some embodiments, $R_2$ has 3 trans double carbon-carbon bonds.

In some embodiments, $R_2$ has 4 trans double carbon-carbon bonds.

In some embodiments, $R_2$ is a $C_{33-40}$ alkyl.

In some embodiments, $R_2$ is a $C_{34-40}$ alkyl.

In some embodiments, $R_2$ is a $C_{35-40}$ alkyl.

In some embodiments, $R_2$ is a $C_{36-40}$ alkyl.

In some embodiments, $R_2$ is $C_{32}$ alkyl.

In some embodiments, $R_2$ is $C_{33}$ alkyl.

In some embodiments, $R_2$ is $C_{34}$ alkyl.

In some embodiments, $R_2$ is $C_{35}$ alkyl.

In some embodiments, $R_2$ is $C_{36}$ alkyl.

In some embodiments, $R_2$ is $C_{37}$ alkyl.

In some embodiments, $R_2$ is $C_{38}$ alkyl.

In some embodiments, $R_2$ is $C_{39}$ alkyl.

In some embodiments, $R_2$ is $C_{40}$ alkyl.

It is understood that the definitions above for $R_1$ and $R_2$ can be combined in any manner.

In some embodiments, $R_{20}$ is an alkenyl having at least 34 carbons and at least one trans double carbon-carbon bond.

In some embodiments, $R_{20}$ is an alkenyl having at least 35 carbons and at least one trans double carbon-carbon bond.

In some embodiments, $R_{20}$ is a $C_{35-45}$ alkenyl having at least one trans double carbon-carbon bond.

In some embodiments, $R_{20}$ is a $C_{36-45}$ alkenyl having at least one trans double carbon-carbon bond.

In some embodiments, $R_{20}$ is a $C_{35-40}$ alkenyl having at least one trans double carbon-carbon bond.

In some embodiments, $R_{20}$ is a $C_{36-40}$ alkenyl having at least one trans double carbon-carbon bond.

In some embodiments, $R_{20}$ has 2 to 4 trans double carbon-carbon bonds.

In some embodiments, $R_{20}$ has 2 trans double carbon-carbon bonds.

In some embodiments, $R_{20}$ has 3 trans double carbon-carbon bonds.

In some embodiments, $R_{20}$ has 4 trans double carbon-carbon bonds.

In some embodiments, $R_{20}$ is a $C_{33-40}$ alkyl.

In some embodiments, $R_{20}$ is a $C_{34-40}$ alkyl.

In some embodiments, $R_{20}$ is a $C_{35-40}$ alkyl.

In some embodiments, $R_{20}$ is a $C_{36-40}$ alkyl.

In some embodiments, $R_{20}$ is $C_{32}$ alkyl.

In some embodiments, $R_{20}$ is $C_{33}$ alkyl.

In some embodiments, $R_{20}$ is $C_{34}$ alkyl.

In some embodiments, $R_{20}$ is $C_{35}$ alkyl.

In some embodiments, $R_{20}$ is $C_{36}$ alkyl.

In some embodiments, $R_{20}$ is $C_{37}$ alkyl.

In some embodiments, $R_{20}$ is $C_{38}$ alkyl.

In some embodiments, $R_{20}$ is $C_{39}$ alkyl.

In some embodiments, $R_{20}$ is $C_{40}$ alkyl.

In some embodiments, the compound of Formula (I) is not one or more of the following compounds:

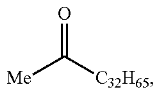, 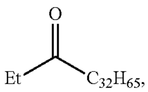,

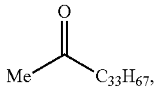, 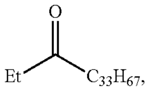,

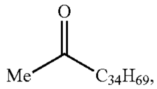, 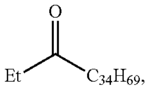,

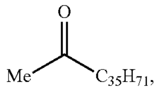, 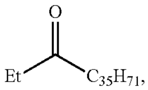,

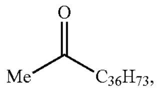, 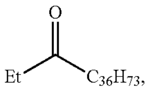,

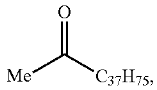, 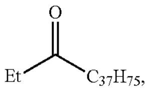,

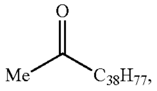, and 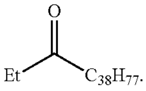.

In some embodiments, the compound of Formula (I) is selected from the group consisting of:

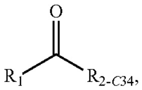, wherein $R_1$ is methyl or ethyl, and $R_{2\text{-}C34}$ is $C_{34}$ alkenyl having 2 or 3 trans double carbon-carbon bonds;

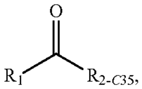, wherein $R_1$ is methyl or ethyl, and $R_{2\text{-}C35}$ is $C_{35}$ alkenyl having 2 or 3 trans double carbon-carbon bonds;

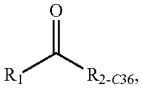, wherein $R_1$ is methyl or ethyl, and $R_{2\text{-}C36}$ is $C_{36}$ alkenyl having 2 or 3 trans double carbon-carbon bonds;

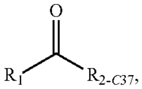, wherein $R_1$ is methyl or ethyl, and $R_{2\text{-}C37}$ is $C_{37}$ alkenyl having 1, 2, 3, or 4 trans double carbon-carbon bonds;

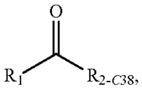, wherein $R_1$ is methyl or ethyl, and $R_{2\text{-}C38}$ is $C_{38}$ alkenyl having 1, 2, 3, or 4 trans double carbon-carbon bonds; and

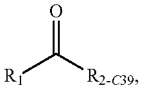, wherein $R_1$ is methyl or ethyl and $R_{2\text{-}C39}$ is $C_{39}$ alkenyl having 1, 2, 3, or 4 trans double carbon-carbon bonds.

In some embodiments, $R_2$ has two or more trans double carbon-carbon bonds, and at least two of the trans double carbon-carbon bonds are spaced from one another by 5 carbon atoms. For example, the compound of Formula (I) can be one or more of

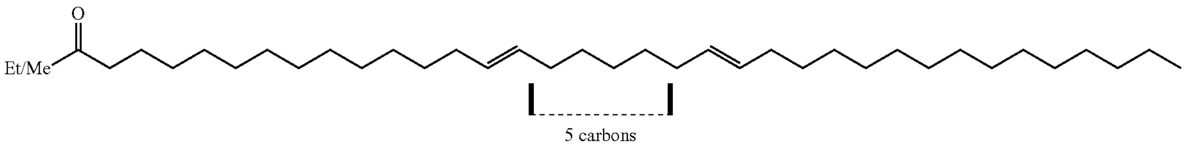,

Me (methyl), 37:2 methyl alkenone
Et (ethyl), 38:2 ethyl alkenone

-continued

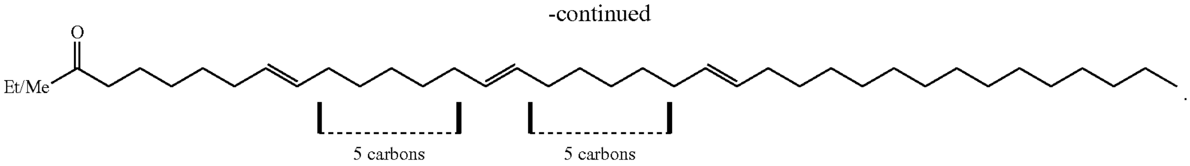

Me (methyl); 37:3 methyl alkenone
Et (ethyl); 38:3 ethyl alkenone

In some embodiments, the composition includes a majority component (e.g., greater than 50% by weight of the total weight of the compounds for formula (I)) including one or more of:

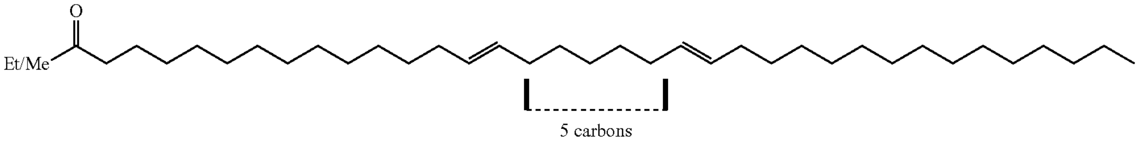

, and

Me (methyl), 37:2 methyl alkenone
Et (ethyl), 38:2 ethyl alkenone

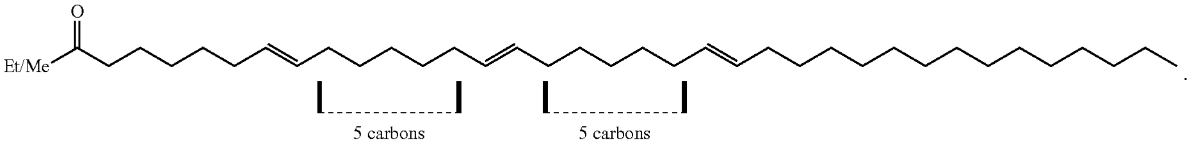

Me (methyl); 37:3 methyl alkenone
Et (ethyl); 38:3 ethyl alkenone

In some embodiments, the composition includes one or more of the following compounds for Formula (I):

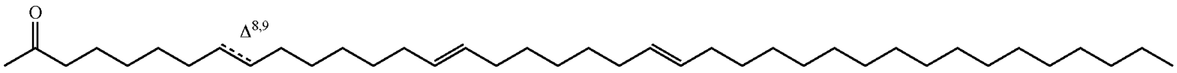

,

39:2 methyl alkenone
$\Delta^{8,9}$, 39:3 methyl alkenone

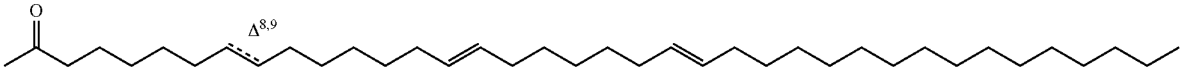

,

38:2 methyl alkenone
$\Delta^{8,9}$, 38:3 methyl alkenone

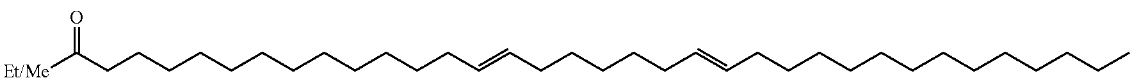

, and

Me (methyl); 36:2 methyl alkenone
Et (ethyl); 37:2 ethyl alkenone

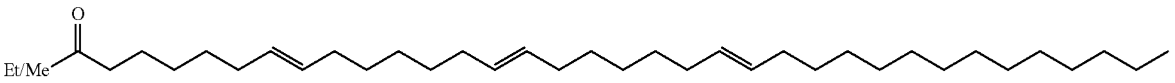

Me (methyl); 36:3 methyl alkenone
Et (ethyl), 37:3 ethyl alkenone

In some embodiments, the compound of formula (I) is one or more of

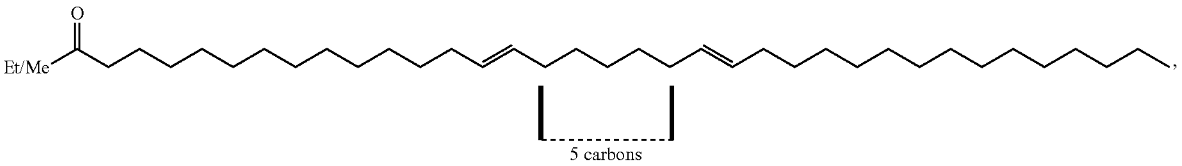

Me (methyl), 37:2 methyl alkenone
Et (ethyl), 38:2 ethyl alkenone

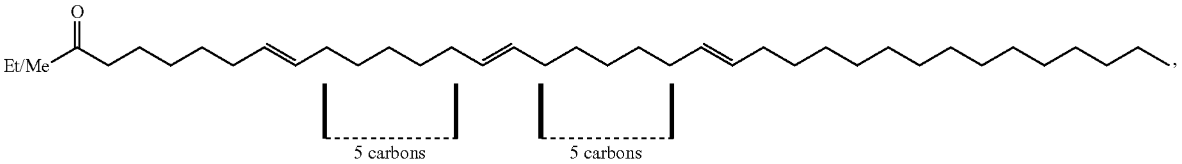

Me (methyl), 37:3 methyl alkenone
Et (ethyl), 38:3 ethyl alkenone

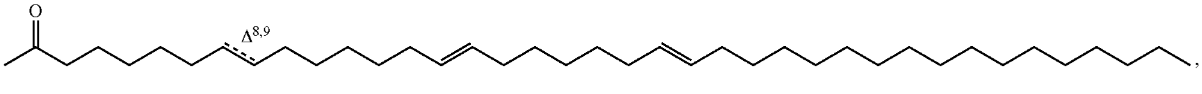

39:2 methyl alkenone
$\Delta^{8,9}$, 39:3 methyl alkenone

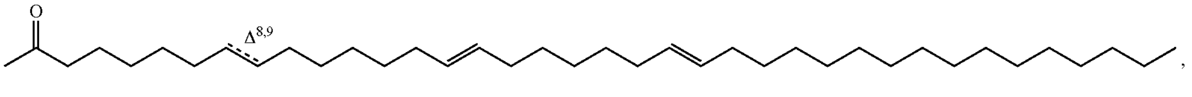

38:2 methyl alkenone
$\Delta^{8,9}$, 38:3 methyl alkenone

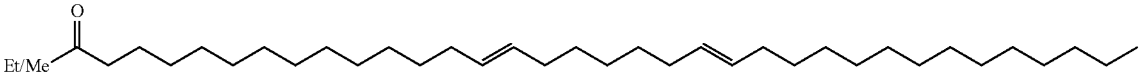
, and

Me (methyl), 36:2 methyl alkenone
Et (ethyl), 37:2 ethyl alkenone

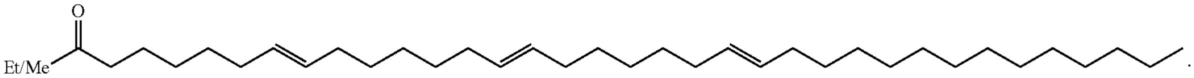

Me (methyl), 36:3 methyl alkenone
Et (ethyl), 37:3 ethyl alkenone

In some embodiments, m is 1 or 2.

In some embodiments, in the compound of Formula (II), (III), or (IV), $R_2$ is independently a $C_{34-45}$ alkenyl having at least one trans double carbon-carbon bond.

In some embodiments, in the compound of Formula (II), (III), or (IV), $R_2$ is independently a $C_{35-45}$ alkenyl having at least one trans double carbon-carbon bond.

In some embodiments, in the compound of Formula (II), (III), or (IV), $R_2$ is independently a $C_{36-45}$ alkenyl having at least one trans double carbon-carbon bond.

In some embodiments, in the compound of Formula (II), (III), or (IV), $R_2$ is independently a $C_{34-40}$ alkenyl having at least one trans double carbon-carbon bond. In some embodiments, in the compound of Formula (II), (III), or (IV), $R_2$ is independently a $C_{35-40}$ alkenyl having at least one trans double carbon-carbon bond.

In some embodiments, in the compound of Formula (II), (III), or (IV), $R_2$ is independently a $C_{36-40}$ alkenyl having at least one trans double carbon-carbon bond.

In some embodiments, in the compound of Formula (II), (III), or (IV), $R_2$ independently comprises 2 to 4 trans double carbon-carbon bonds.

In some embodiments, in the compound of Formula (II), (III), or (IV), $R_2$ independently comprises 3 trans double carbon-carbon bonds.

In some embodiments, in the compound of Formula (II), (III), or (IV), $R_2$ is independently selected from:

$C_{34}$ alkenyl having 2 or 3 trans double carbon-carbon bonds;

$C_{35}$ alkenyl having 2 or 3 trans double carbon-carbon bonds;

$C_{36}$ alkenyl having 2 or 3 trans double carbon-carbon bonds;

$C_{37}$ alkenyl having 1, 2, 3, or 4 trans double carbon-carbon bonds;

$C_{38}$ alkenyl having 1, 2, 3, or 4 trans double carbon-carbon bonds; and $C_{39}$ alkenyl having 1, 2, 3, or 4 trans double carbon-carbon bonds.

In some embodiments, in the compound of Formula (II), (III), or (IV), $R_2$ is independently selected from:

$R_2$ is $C_{34}$ alkenyl having 2 or 3 trans double carbon-carbon bonds;

$R_2$ is $C_{35}$ alkenyl having 2 or 3 trans double carbon-carbon bonds;

$R_2$ is $C_{36}$ alkenyl having 2 or 3 trans double carbon-carbon bonds;

$R_2$ is $C_{37}$ alkenyl having 1, 2, 3, or 4 trans double carbon-carbon bonds;

$R_2$ is $C_{38}$ alkenyl having 1, 2, 3, or 4 trans double carbon-carbon bonds; and $R_2$ is $C_{39}$ alkenyl having 1, 2, 3, or 4 trans double carbon-carbon bonds.

In some embodiments, $R_2$ has two or more trans double carbon-carbon bonds, and at least two of the trans double carbon-carbon bonds are separated from one another by 5 carbon atoms. For example, $R_2$ in the compounds of Formula (II), Formula (III), or Formula (IV) can independently selected from In some embodiments, $R_{11}$, $R_{12}$, and $R_{13}$ are each independently selected from H and $C_{1-6}$ alkyl.

In some embodiments, $R_{11}$, $R_{12}$, and $R_{13}$ are each independently selected from H and methyl.

In some embodiments, $R_{11}$, $R_{12}$, and $R_{13}$ are each H.

In some embodiments, $R_{14}$, $R_{15}$, $R_{16}$, $R_{17}$, and $R_{18}$ are each independently selected from H, $C_{1-6}$ alkyl, and halo.

In some embodiments, $R_{14}$, $R_{15}$, $R_{16}$, $R_{17}$, and $R_{18}$ are each independently selected from H and $C_{1-6}$ alkyl.

In some embodiments, $R_{14}$, $R_{15}$, $R_{16}$, $R_{17}$, and $R_{18}$ are each independently selected from H and methyl.

In some embodiments, $R_{14}$, $R_{15}$, $R_{16}$, $R_{17}$, and $R_{18}$ are each H.

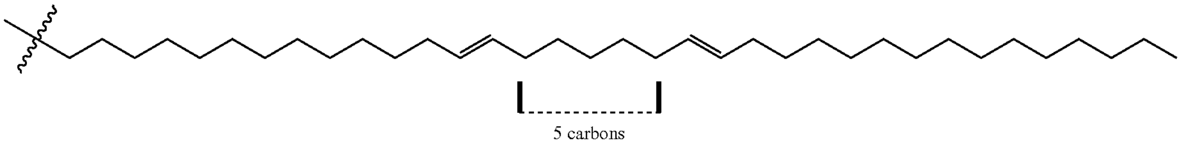

,

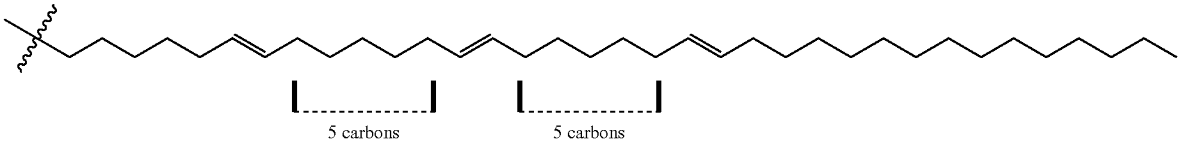

,

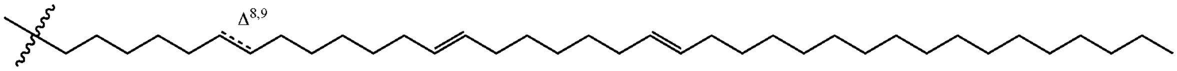

,

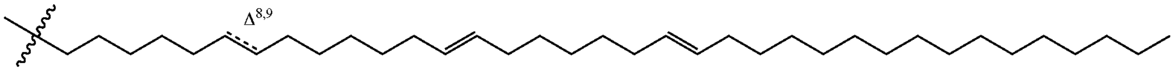

,

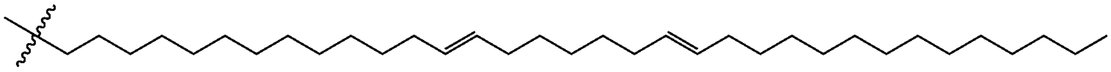
, and

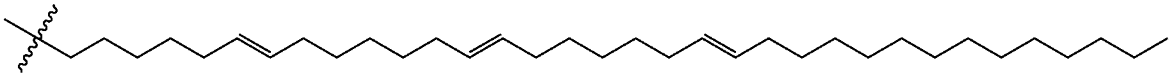
.

In some embodiments, in the compound of Formula (II), (III), or (IV), $R_2$ is $C_{30-45}$ alkyl (e.g., $C_{34-45}$ alkyl, $C_{35-45}$ alkyl, $C_{36-45}$ alkyl, $C_{37-45}$ alkyl, $C_{38-45}$ alkyl, $C_{39-45}$ alkyl, $C_{40-45}$ alkyl, $C_{34}$ alkyl, $C_{35}$ alkyl, $C_{36}$ alkyl, $C_{37}$ alkyl, $C_{38}$ alkyl, $C_{39}$ alkyl, or $C_{40}$ alkyl).

In some embodiments, n is an integer of from 1 to 100 (e.g., 1 to 50, 1 to 20, 1 to 10, 1 to 5, 5 to 50, 5 to 20, 5 to 10, 10 to 50, or 10 to 20).

In some embodiments, $R_4$, $R_5$, and $R_6$ are each independently selected from H, $C_{1-6}$ alkyl, and halo.

In some embodiments, $R_4$, $R_5$, and $R_6$ are each independently selected from H and $C_{1-6}$ alkyl.

In some embodiments, $R_4$, $R_5$, and $R_6$ are each independently selected from H and methyl.

In some embodiments, $R_4$, $R_5$, and $R_6$ are each H.

In some embodiments, $R_8$ is selected from $—PO_2—OR_9$ and $—CONHR_{10}$, wherein $R_9$ is $—CH_2CH_2N^+R_{11}R_{12}R_{13}$, wherein $R_{11}$, $R_{12}$, and $R_{13}$ are each independently selected from H, $C_{1-6}$ alkyl, $C_{1-6}$ haloalkyl, and halo, and $R_{10}$ is $—(CH_2)_mSO_3—$, $—(CH_2)_mN^+R_{14}R_{15}CH_2CO_2—$, $—(CH_2)_mN^+R_{16}R_{17}R_{18}$, wherein m is an integer of from 1 to 10; $R_{14}$, $R_{15}$, $R_{16}$, $R_{17}$, and $R_{18}$ are each independently selected from H, $C_{1-6}$ alkyl, $C_{1-6}$ haloalkyl, and halo.

In some embodiments, $R_{11}$, $R_{12}$, and $R_{13}$ are each independently selected from H, $C_{1-6}$ alkyl, and halo.

In some embodiments, the compound of Formula (I), (II), (III), or (IV) has a melting temperature of 70° C. or less (e.g., 60° C. or less, 50° C. or less, 40° C. or less, or 30° C.).

In some embodiments, the compound of Formula (I), (II), (III), or (IV) is a waxy solid at 25° C. In some embodiments, the compound of Formula (I), (II), (III), or (IV) is a waxy solid at 30° C. (e.g., 40° C., 50° C., 60° C., 70° C., or 80° C.).

In some embodiments, the composition is in the form of a topical composition, such as a skin-care composition, a hair-care composition, and/or a cosmetic composition.

In some embodiments, the compound of Formula (I), (II), (III), or (IV) functions as an emollient, an abrasive, an occlusive agent, an encapsulating agent, a stabilizing agent, a binding agent, a thickening agent, a surfactant, an antimicrobial agent, or any combination thereof.

In some embodiments, the compound of Formula (I), (II), (III), or (IV) is present from 1 to 50% w/w (e.g., from 1 to 40%, from 1 to 30%, or from 1 to 20%) of the total composition.

In some embodiments, the compound of Formula (I), (II), (III), or (IV) is isolated from algae such as Isochrysis, Emiliania huxleyi, and/or Gephyrocapsa oceanica, or derived (i.e., through chemical synthesis) from the algae-isolated compound of Formula (I), (II), (III), or (IV).

In some embodiments, the polar head group R19 is an alcohol, an ester, an acid, a carboxylate, a sulfonate, a phosphonate, and/or ammonium.

In some embodiments, the composition does not include any petroleum-based waxes or oils, plant-based fats, animal-based fats, and/or any combination thereof. For example, the alkenone or the alkenone derivative in the composition can be solely derived from an algae such as *Isochrysis, Emiliania huxleyi*, and/or *Gephyrocapsa oceanica.*

In some embodiments, the composition further includes an oil, a fatty acid, or both. In some embodiments, the composition further includes a surfactant such as a $C_{4-28}$ fatty acid carboxylate, a $C_{4-28}$ alkyl sulfate, a $C_{4-28}$ alkyl betaine, and/or an alkenone-derived surfactant.

In some embodiments, the compositions of the present disclosure further include a synthetic agent selected from synthetic solubilizing agents, synthetic emulsifying agents, synthetic humectants, synthetic emollients, synthetic occlusive agents, synthetic surfactants, synthetic preservatives, synthetic binding agents, synthetic thickeners, synthetic solvents, synthetic fragrances, and any combination thereof In some embodiments, the compositions of the present disclosure further include a naturally occurring agent selected from natural emollients, natural occlusive agents, natural emulsifying agents, natural anti-oxidants, natural colorants, natural fragrances, and any combination thereof.

In some embodiments, the composition further includes one or more mono-, di-, or triglycerides and/or one or more alcohols. In some embodiments, the composition is an encapsulant.

In some embodiments, the one or more compounds of the present disclosure are purified (e.g., whitened by, for example, decolorizing with activated charcoal) prior to incorporation into the composition.

In some embodiments, the compositions of the present disclosure do not include any petroleum-based waxes or oils, plant-based fats, animal-based fats, and/or any combination thereof. For example, the alkenone or the alkenone derivative in the compositions of the present disclosure can be solely derived from an algae such as *Isochrysis, Emiliania huxleyi*, and/or *Gephyrocapsa oceanica.*

In some embodiments, the compositions of the present disclosure further include an oil (e.g., an acylglycerol), a fatty acid, or both. In some embodiments, the composition further includes a surfactant such as a $C_{4-28}$ fatty acid carboxylate, a $C_{4-28}$ alkyl sulfate, a $C_{4-28}$ alkyl betaine, and/or an alkenone-derived surfactant.

In some embodiments, the compounds of Formula (I), Formula (II), Formula (III) and/or Formula (IV) are present from 1 to 50% w/w (e.g., from 1 to 40%, from 1 to 30%, or from 1 to 20%) of the total alkenone or alkenone-derivative content in the composition.

As will be explained in greater detail below, in certain embodiments, the compositions of the present disclosure are emollients. The compositions of the present disclosure can further include a surfactant (a fatty acid carboxylate, a sulfate, a betaine, and/or an alkenone-derived surfactant). For example, a given composition can be a skin cleanser.

Compositions Containing Alkenones and/or Alkenone-Derived Compounds

This compositions of the present disclosure use unique but abundant algal lipids to address growing concerns about the use of petroleum not only for fuels, but other products such as those in personal care and related industries to feed a burgeoning market for "green" non-petroleum products. Topical compositions including the compounds of the present disclosure include emulsions that can be generally divided into three categories, based on viscosity: low viscosity lotions, medium viscosity creams, and high viscosity ointments. Examples of products include abrasive soaps, with alkenones and/or alkenone-derived compounds serving as natural exfoliating agents. Alkenones and their derivatives in these compositions can serve as emollients, occlusive agents, encapsulating agents, stabilizing agents, binding agents, thickening agents, surfactants, and antimicrobials. Other roles for alkenones include providing products with desired textural, tactile, and aesthetic qualities, all of which have historically been achieved with petroleum.

The personal care composition can be a skin care, antiperspirant, deodorant, cosmetic, or hair care product. The personal care composition can be used as, for example, a moisturizer, conditioner, anti-aging compound, skin lightener, sunscreen, sunless tanner, shave preparation, lipstick, foundation, mascara, after-shave, and combinations thereof In certain embodiments, the composition is applied to the face, neck, hands, arms, and other typically exposed areas of the body.

The personal care composition can be in a wide variety of forms. Non-limiting examples include simple solutions (e.g., water or oil based), dispersions, and emulsions. The personal care composition can be substantially anhydrous (i.e., the composition comprises no more than about 1%, 0.5%, or, 0% water). The personal care compositions can be fluid or solid (gels, sticks, flowable solids, amorphous materials). In certain embodiments, the personal care composition is in the form of an emulsion. Emulsion can be generally classified as having a continuous aqueous phase (e.g., oil-in-water and water-in-oil-in-water) or a continuous oil phase (e.g., water-in-oil and oil-in-water-in-oil).

The compositions of the present disclosure can include a variety of other components in addition to the alkenone and/or alkenone-derived compounds. For example, the compositions can include solubilizing agents, emulsifying agents, humectants, emollients, occlusive agents, surfactants, preservatives, binding agents, thickeners, solvents, antioxidants, colorants, and/or fragrances; each of which can be naturally occurring or man-made (i.e., synthetic).

Synthetic Components

Examples of synthetic solubilizing agents include alkyl and acyl glucosides, polyethylene glycols, and polysaccharides.

Examples of synthetic emulsifying agents include fatty alcohol (C8-C20) (poly)glucosides, (poly)glyceryl fatty alcohols, polyethylene fatty alcohols, fatty acid (poly)glucosides, (poly)glyceryl fatty acids, and polyhydroxy fatty acids.

Examples of synthetic humectants include propylene glycol, butylene glycol, and pentylene glycol.

Examples of synthetic emollients include fatty alcohol esters (e.g., cetearyl ethylhexanoate, isoamyl cocoate, isoamyl laurate), polyglyceryl fatty acids (e.g., polyglyceryl-6-stearate), and polyglyceryl sebecates.

Examples of synthetic occlusive agents include siloxanes, sodium hyaluronate, and hydrolyzed polyglutamic acids.

Examples of synthetic surfactants include sodium lauryl sarcosinate, and fatty alcohol glucosides (e.g., caprylyl-capryl glucoside).

Examples of synthetic preservatives include phenoxyethanol, benzyl alcohol, glycerol ethers, and alkylparabens.

Examples of synthetic binding agents include EDTA and sodium phytate.

Examples of synthetic thickeners include polyacrylates (carbomer), propylene glycol, and siloxanes.

Examples of synthetic solvents include ethylene glycol and propylene glycol,

Examples of synthetic fragrances include aldehydes and esters.

Natural Components

Examples of natural emollients include lanolin, allantoin, shea butter, and trehalose.

Examples of natural occlusive agents include glycerin, citric acid, and mineral oil.

Examples of natural emulsifying agents include triglycerides and lecithin.

Examples of natural anti-oxidants include tocopherol.

Examples of natural colorants include clays.

Examples of natural fragrances include botanical extracts.

Carriers, Emulsifiers

In some embodiments, the personal care composition can include a carrier. Carriers can be selected for various stability, aesthetics, and/or compatibility with other materials present in the personal care composition.

Suitable carriers include water and/or water soluble solvents. The personal care composition can include from about 1% to about 95% by weight of water and/or water-equivalent solvent. The composition can include from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% water and/or a water-equivalent solvent. "Water-equivalent solvent" refers to a compound which has a similar ability as water to solubilize a material. Suitable water-equivalent solvents include monohydric alcohols, dihydric alcohols, polyhydric alcohols, glycerol, glycols, polyalkylene glycols such as polyethylene glycol, and mixtures thereof. Examples of suitable solvents include lower aliphatic alcohols such as ethanol, propanol, butanol, isopropanol; diols such as 1,2-propanediol, 1,3-propanediol, butanediol, pentanediol, hexanediol, heptanediol, decanediol; glycerin; water, and mixtures thereof In certain embodiments, the personal care includes comprises water, diols, glycerin, and combinations thereof.

Suitable carriers also include oils. The personal care composition can include from about 1% to about 95% by weight of one or more oils. The composition can include from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% of one or more oils. Oils can be used to solubilize, disperse, or carry materials that are not suitable for water or water-equivalent solvents. Suitable oils include silicones, hydrocarbons, esters, fatty amides, ethers, and mixtures thereof. Oils can be fluid at room temperature. However, certain personal care product forms (i.e., solid or semi-solid stick) can include non-fluid oils. The oils can be volatile or nonvolatile. "Non-volatile" means a material that exhibits a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C. Volatile oils can be used to provide a lighter feel when a heavy, greasy film is undesirable.

Suitable oils include volatile oils. In certain embodiments, the volatile oils can have a viscosity ranging from about 0.5 to about 5 centistokes 25° C. Volatile oils can be used to promote more rapid drying of the skin care composition after it is applied to skin. Nonvolatile oils are also suitable for use in the composition. Nonvolatile oils can be used for emolliency and protective properties. Nonvolatile oils can have a viscosity ranging from about 5 to about 800,000 cst (or greater) or from about 20 to about 200,000 cst.

Suitable silicone oils include polysiloxanes. Polylsiloxanes can have a viscosity of from about 0.5 to about 1,000,000 centistokes at 25° C. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500, 100,000, and 300,000 centistokes.

Suitable hydrocarbon oils include straight or branched chain alkanes and alkenes. The chain length can be selected based on desired functional characteristics such as volatility. Suitable hydrocarbon oils can have between 5-20 carbon atoms or, alternately, between 8-16 carbon atoms. Suitable hydrocarbons include pentane, hexane, heptane, decane, dodecane, tetradecane, tridecane, and $C_{8-20}$ isoparaffins. Suitable hydrocarbons include isooctane, isododecane, isohexadecane, isoeicosane by Permethyl Corporation under the tradename Permethyl®. Suitable hydrocarbon oils can have greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof.

Other suitable oils include esters. Suitable esters typically contain at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof caninclude or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate. Other suitable esters are further described in the Personal Care Product Council's *International Cosmetic Ingredient Dictionary and Handbook*, Thirteenth Edition, 2010, under the functional category of "Esters."

Other esters suitable for use in the personal care composition include mono-carboxylic acid esters such as $C_{12-15}$ alkyl benzoate.

Other esters suitable for use in the personal care composition include di- and tri-alkyl and alkenyl esters of carboxylic acids, such as esters of $C_4$ to $C_8$ dicarboxylic acids (e.g., $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, dibutyl adipate, and tristearyl citrate.

Other esters suitable for use in the personal care composition include those known as polyhydric alcohol esters.

Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters.

Still other esters suitable for use in the personal care composition include glycerides, including, but not limited to, mono-, di-, and tri-glycerides. For example, the glycerides can be mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, sweet almond oil, apricot kernel oil, camelina sativa oil, rapeseed oil, tamanu seed oil, linseed oil, coconut oil, lanolin oil, soybean oil, and the like. Synthetic oils include, but are not limited to, triolein and tristearin glyceryl dilaurate. Other glyceryl esters of fatty acids include fatty acid mono-, di-, and triglycerides which are natural fats or oils that have been modified such as glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and the like.

Other suitable oils include fatty amides. Fatty amides include compounds having an amide functional group while being liquid at 25° C. and insoluble in water, such as N-acetyl-N-butylaminopropionate, isopropyl N-lauroylsarcosinate, and N,N,-diethyltoluamide. Other suitable fatty amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

Emulsifiers

The personal care compositions can include an emulsifier. An emulsifier is particularly suitable when the composition is in the form of an emulsion or if immiscible materials are being combined. The skin care composition can include from about 0.05%, 0.1%, 0.2%, 0.3%, 0.5%, or 1% to about 20%, 10%, 5%, 3%, 2%, or 1% emulsifier. Emulsifiers can be nonionic, anionic or cationic. Non-limiting examples of emulsifiers are described in McCutcheon's, *Emulsifiers and Detergents,* 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifying ethers and esters include ethers of polyglycols and of fatty alcohols—including saturated or unsaturated $C_{12-30}$ alcohols (e.g., oleyl alcohol, cetyl alcohol, stearyl alcohol or behenyl alcohol) and polyglycols comprising n number of oxyalkylene groups wherein n is an integer from 1 to 200 or, alternately, from 2 to 30 (e.g., 1 to 20 oxyethylene groups). Examples of emulsifying ethers and esters include compounds with the INCI names of steareth-n, beheneth-n or oleth-n. In some embodiments, examples include compounds having the INCI names steareth-8, steareth-10, steareth-16, steareth-20, ceteth-10, laureth-4, laureth-3, trideceth-6, ceteareth-5, oleth-10, and beneth-10.

Emulsifiers can include esters of polyglycols and of fatty acids—including saturated or unsaturated $C_{12-30}$ fatty acids (e.g., oleic acid, cetylic acid, stearic acid) and polyglycols comprising n number of oxyalkylene groups wherein n is an integer from 1 to 200 or alternately, 1 to 50 (e.g., 1 to 20 oxyethylene groups). Examples include compounds with the INCI name PEG-n stearate or PEG-n oleate). In some embodiments, examples include polyethylene glycol-8 monostearate, polyethylene glycol-10, or polyethylene glycol-12 distearate.

Emulsifiers can include ethers of polyglycols and of fatty alcohols which are glycosylated—including $C_{12-30}$ alcohols having from 1 to 10 glycosyl groups and polyglycols comprising n number of oxyalkylene groups wherein n is an integer from 1 to 200 (e.g., 1 to 20 oxyethylene groups). A suitable example includes polyoxyethylenated (20 OE) methyl glucose distearate.

Examples of emulsifiers include esters of polyglycols and of fatty acids which are glycosylated—including $C_{12-30}$ fatty acids having from 1 to 10 glycosyl groups and polyglycols comprising n number of oxyalkylene groups wherein n is an integer from 1 to 200 (e.g., 1 to 20 oxyethylene groups).

Examples of emulsifiers include ethers of $C_{12-30}$ alcohols and of glycerol or of polyglycerol—A suitable example includes polyglyceryl-3 cetyl ether, such as Chimexane NL from Chimex.

Examples of emulsifiers include esters of $C_{12-30}$ fatty acids and of glycerol or of polyglycerol—including esters comprising from 1 to 10 glycerol groups. Examples include hexa-glyceryl monosterate, diglyceryl distearate, tetraglyceryl tristearate, decaglyceryl decastearate, diglyceryl monostearate, hexaglyceryl tristearate, decaglyceryl pentastearate, the ester of glycerol and of palmitic and stearic acids, and glyceryl mono- and dibehenate.

Examples of emulsifiers include ethers of oxyalkylene-modified $C_{12-30}$ alcohols and of glycerol or polyglycerol.

Examples of emulsifiers include ethers of $C_{12-30}$ fatty alcohols comprising and of sucrose or glucose—Suitable examples include compounds with the INCI names of $C_{12-18}$ alkylglucoside, $C_{12-20}$ alkylglucoside (e.g., Montanov L from Seppic), cetearyl glucoside (e.g., a mixture with cetearyl alcohol under the reference Montanov 68 from Seppic), myristyl glucoside (e.g., a mixture with myristyl alcohol under the reference Montanov 14 from Seppic) or cetearyl glucoside (e.g., Tegocare CG 90 from Evonik Goldschmidt), Examples of emulsifiers include esters of sucrose and of $C_{12-30}$ fatty acids, such as sucrose distearate or sucrose tristearate, sucrose cocoate, sucrose dilaurate, sucrose distearate, sucrose hexaerucate, sucrose hexapalmitate, sucrose laurate, sucrose mortierellate, sucrose myristate, sucrose oleate, sucrose palmitate, sucrose pentaerucate, sucrose polybehenate, sucrose polycottonseedate, sucrose polylaurate, sucrose polylinoleate, sucrose polyoleate, sucrose polypalmate, sucrose polysoyate, sucrose polystearate, sucrose ricinoleate, sucrose stearate, sucrose tetraisostearate, and sucrose trilaurate. A suitable example includes the mixture of esters (mono- and polyesters) of stearic acid and of sucrose sold as Crodesta Fl 10 by Croda.

Examples of emulsifiers include esters of pentaerythritol and of $C_{12-30}$ fatty acids, such as pentaerythritol tetrastearate.

Examples of emulsifiers include esters of sorbitol and/or of sorbitan and of $C_{12-30}$ fatty acids, such as sorbitan monostearate, sorbitan tristearate, or sorbitan laurate, such as Span 20 from Uniqema, Examples of emulsifiers include ethers of sorbitol and/or of sorbitan and of alkoxylated sorbitan—Suitable examples include sorbeth-8 beeswax or sorbeth-20 beeswax from Nikko Chemical.

Examples of emulsifiers include esters of $C_{12-30}$ fatty acids and of alkoxylated ethers of sorbitol and/or of Suitable examples include polysorbate-60, polysorbate-61, sorbeth-3 isostearate, polyoxyethylenated 4 OE sorbitan monostearate, and polyoxyethylenated 20 OE sorbitan tristearate.

Structuring Agent

The personal care composition can include a structuring agent to increase viscosity, thicken, solidify, or provide solid or crystalline structure to the personal care composition. Examples of aqueous or water structuring agents include polymeric agents, natural or synthetic gums, polysaccharides, and the like. In one embodiment, the composition can include from about 0.0001%, 0.001%, 0.01%, 0.05%, 0.1%, 0.5%, 1%, 2%, 3%, or 5% to about 25%, 20%, 10%, 7%, 5%, 4%, or 2%, by weight of the composition, of one or more structuring agents.

Polysaccharides and gums can be used as aqueous phase thickening agents. Classes of polymeric structuring agents include but are not limited to carboxylic acid polymers (e.g., carbomers), polyacrylamide polymers, sulfonated polymers, high molecular weight polyalkylglycols or polyglycerins, copolymers thereof, hydrophobically modified derivatives thereof (e.g., oil structuring agents, silicone elastomers, silicone gums, silicone waxes), and mixtures thereof.

Other structuring agents are natural or synthetic montmorillonite minerals such as hectorite, bentonite, and quaternized derivatives thereof, which are obtained by reacting the minerals with a quaternary ammonium compound (e.g., stearalkonium bentonite and stearalkonium hectorite); and silicas, silicates, silica silylate, and alkali metal or alkaline earth metal derivatives thereof.

Optional Personal Care Ingredients

The personal care compositions can include one or more optional components to provide an efficacious and/or consumer desirable product. For example, the composition can include sugar amines, vitamins, oil control agents, photosterols, hexamidine compounds, tightening agents, anti-wrinkle actives, anti-atrophy actives, flavonoids, N-acyl amino acid compounds, retinoids, peptides, particulate materials, UV actives, photostabilizers, anti-cellulite agents, desquamation actives, anti-acne actives, anti-oxidants, radical scavengers, conditioning agents, botanical extracts, preservatives, and/or detersive surfactants, and combinations thereof.

Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). In some embodiments, the sugar amine is glucosamine, such as D-glucosamine and N-acetyl glucosamine. In certain embodiments, the sugar amine is N-acetyl-D-glucosamine.

Examples of vitamins include: vitamin B compounds (including B1 compounds, B2 compounds, B3 compound, B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of vitamin A, including retinoids, retinol, retinyl acetate, retinyl palmitate, retinoic acid, retinaldehyde, retinyl propionate, carotenoids (pro-vitamin A), and other compounds which possess the biological activity of vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids.

Examples of suitable oil control agents include salicylic acid, dehydroacetic acid, benzoyl peroxide, vitamin B3 compounds, their isomers, esters, salts and derivatives, and mixtures thereof. Examples of oil absorbing materials include starch, calcium silicate, polyethylene, nylon, boran nitride, mica, clays such as bentonite, montmarrillonite and kaolin, zeolite, cyclodextrins, fumed silica, synthetic clays such as polymer powders including natural, synthetic, and semisynthetic cellulose, fluorocarbon resins, polypropylene, modified starches of cellulose acetate, particulate cross-linked hydrophobic acrylate or methacrylate copolymers and mixtures thereof. In one embodiment, the personal care composition can include from about 0.001%, 0.01%, 0.05%, 0.1%, 0.5%, or 1% to about 25%, 20%, 10%, 7%, 5%, or 3% by weight of the composition, of one or more oil control agents.

Examples of phytosterols include β-sitosterol, campesterol, brassicasterol, Δ5-avennasterol, lupenol, α-spinasterol, stigmasterol, their derivatives, analogs, and combinations thereof. In one embodiment, the composition can include from about 0.0001%, 0.001%, 0.01%, 0.05%, 0.1%, 0.5%, or 1% to about 25%, 20%, 10%, 7%, 5%, or 3%, by weight of the composition, of one or more phytosterol.

In some embodiments, the personal care composition includes a tightening agent. A tightening agent is a compound capable of having a tightening effect on keratinous tissues and, typically, on skin. Examples of tightening agents can include plant or animal proteins and their hydrolysates such as maize, rye, wheat, buckwheat, sesame, spelt, pea, bean, lentil, soybean and lupin; polysaccharides of natural origin including (i) polyholosides, for example, in the form of starch derived especially from rice, maize, potato, cassaya, peas, wheat, oats, etc., or in the form of carrageenans, alginates, agars, gellans, cellulose polymers and pectins, advantageously as an aqueous dispersion of gel microparticles, and (ii) lattices composed of shellac resin, gum sandarac, dammars, elemis, copals, cellulose compounds, and mixtures thereof; mixed silicates including phyllosilicates (e.g., laponites); colloidal particles of inorganic fillers such as silica/alumina colloidal particles such as those sold under then tradename LUDOX® by W.R. Grace & Co.; synthetic polymers such as polyurethane lattices or acrylic/silicone lattices (e.g., propylthio(polymethyl acrylate)), propylthio(polymethyl methacrylate) and propylthio(polymethacrylic acid) grafted polydimethylsiloxane, propyl-thio (polyisobutyl methacrylate) and propylthio(polymethacrylic acid) grafted polydimethylsiloxane (available under the tradenames VS 80, VS 70 and L021 from 3M); and mixtures thereof. The personal care composition can include from about 0.0001%, 0.001%, 0.01%, 0.05%, 0.1%, 0.5%, or 1% to about 30%, 25%, 20%, 10%, 7%, 5%, or 3% by weight of the composition, of one or more tightening agent.

Exemplary anti-wrinkle/anti-atrophy actives include dialkanoyl hydroxyproline compounds, hydroxy acids (e.g., glycolic acid, lactic acid, lactobionic acid), keto acids (e.g., pyruvic acid), phytic acid, lysophosphatidic acid, stilbenes, cinnamates, resveratrol, kinetin, zeatin, dimethylaminoethanol, peptides from natural sources (e.g., soy peptides), and salts of sugar acids (e.g., Mn gluconate, Zn gluconate). In one embodiment, the composition can include from about 0.0001%, 0.001%, 0.01%, 0.05%, 0.1%, 0.5%, or 1% to about 30%, 25%, 20%, 10%, 7%, 5%, or 3% by weight of the composition, of one or more anti-wrinkle/anti-atrophy compounds.

The compositions of the present invention can comprise a flavonoid compound, such as flavones, isoflavones, coumarins, chromones, dicoumarols, chromanones, chromanols, isomers (e.g., cis/trans isomers) thereof, and mixtures thereof In one embodiment, the composition includes from about 0.0001%, 0.001%, 0.01%, 0.05%, 0.1%, 0.5%, or 1% to about 30%, 25%, 20%, 10%, 7%, 5%, or 3%, by weight of the composition, of one or more flavonoid compounds.

Examples of N-acyl amino acid compound include N-acyl Phenylalanine, N-acyl Tyrosine, their isomers, their salts, and derivatives thereof, such as N-undecylenoyl-L-phenylalanine. In one embodiment, the composition can include from about 0.0001%, 0.001%, 0.01%, 0.05%, 0.1%, 0.5%, or 1% to about 30%, 25%, 20%, 10%, 7%, 5%, or 3%, by weight of the composition, of one or more N-acyl amino acids.

In one embodiment, the composition can include from about 0.0001%, 0.001%, 0.01%, 0.05%, 0.1%, 0.5%, or 1% to about 30%, 25%, 20%, 10%, 7%, 5%, or 3%, by weight of the composition, of one or more retinoids. As used herein, “retinoid” includes natural and/or synthetic analogs of Vitamin A or retinol-like compounds which possess the biological activity of Vitamin A in the skin as well as the geometric isomers and stereoisomers of these compounds. The retinoid can include retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), or mixtures thereof. Other retinoids include tocopheryl-retinoate [tocopherol ester of retinoic acid (trans- or cis-), adapalene (6-[3-(1-adamantyl)-4-methoxyphenyl]-2-naphthoic acid}, and tazarotene (ethyl 6-[2-(4,4-dimethylthiochroman-6-yl)-ethynyl]nicotinate).

Examples of peptides can include, but are not limited to, di-, tri-, tetra-, penta-, and hexa-peptides and derivatives thereof In one embodiment, the compositions include from about $1\times10^{-7}$% to about 20%, from about $1\times10^{-6}$% to about 10%, or from about $1\times10^{-5}$% to about 5%, by weight of a peptide. In one embodiment, the composition includes from about 0.0001%, 0.001%, 0.01%, 0.05%, 0.1%, 0.5%, or 1% to about 25%, 20%, 10%, 7%, 5%, 3%, by weight of the composition, of one or more peptides. As used herein, “peptide” refers to peptides containing ten or fewer amino acids and their derivatives, isomers, and complexes with other species such as metal ions (e.g., copper, zinc, manganese, magnesium, and the like). Peptide refers to both naturally occurring and synthesized peptides. Examples of peptides include the dipeptide carnosine (beta-ala-his), the tripeptide gly-his-lys, the tripeptide his-gly-gly, the tripeptide gly-gly-his, the tripeptide gly-his-gly, the tetrapeptide gly-gln-pro-arg, the pentapeptide lys-thr-thr-lys-ser, lipophilic derivatives of peptides, and metal complexes of the aforementioned (e.g., copper complex of the tripeptide his-gly-gly (also known as Iamin)). Other suitable peptides include Peptide CK (arg-lys-arg); Peptide CK+ (ac-arg-lys-arg-NH2); and Peptide E, arg-ser-arg-lys.

Examples of particulate materials useful in the present disclosure include colored and uncolored pigments, interference pigments, inorganic powders, organic powders, composite powders, optical brightener particles, and combinations thereof In one embodiment, the composition includes from about 0.0001%, 0.001%, 0.01%, 0.05%, 0.1%, 0.5%, 1%, or 2% to about 50%, 25%, 20%, 10%, 7%, 5%, or 3% by weight of the composition, of particulate(s).

Examples of inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example $TiO_2$, ZnO, or $ZrO_2$, are commercially available from a number of sources. One example of a suitable particulate material contains the material available from U.S. Cosmetics (TRONOX TiO 2 series, SAT-T CR837, a rutile $TiO_2$). Suitable pigments include charged dispersions of titanium dioxide, as are disclosed in U.S. Pat. No. 5,997,887.

The compositions can contain a UV active, such as sunscreen agents and physical sunblocks. Suitable UV actives can be organic or inorganic. Suitable UV actives are listed in the functional category of “Sunscreen Agents” in the Personal Care Product Council’s *International Cosmetic Ingredient Dictionary and Handbook*, Thirteenth Edition, 2010. Examples of UV actives include 2-ethylhexyl-p-methoxycinnamate, 4-tert-butyl-4'-methoxy dibenzoylmethane, 2-hydroxy-4-methoxybenzo-phenone, 2-phenylbenzimidazole-5-sulfonic acid, octocrylene, zinc oxide, titanium dioxide, and mixtures thereof.

Examples of photostabilizer include ethylhexyl methoxycrylene, or 2-ethylhexyl 2-cyano-3-(4-methoxyphenyl)-3-phenylpropenoate; diethylhexyl 2,6-naphthalate, ethyl-alpha-cyano-3,5-dimethoxy-4-hydroxy cinnamate, ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethyl hexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, di dodecyl-3,5 -dimethoxy-4-hydroxy benzylidene malonate, dipalmitoyl-3,5-dimethoxy-4-hydroxy benzylidene malonate, and di-isopropyl-3,5-dimethoxy-4-hydroxy benzylidene malonate. In one embodiment, the composition can include from about 0.0001%, 0.001%, 0.01%, 0.05%, 0.1%, 0.5%, or 1% to about 30%, 25%, 20%, 10%, 7%, or 5%, by weight of the composition, of one or more suitable photostabilizer.

Examples of anti-cellulite agents include caffeine, theophylline, theobromine, aminophylline, chloroethyltheophylline, dyphylline, etamiphylline, proxyphylline; extracts of tea, coffee, guarana, mate, cola (*Cola nitida*); extracts of climbing ivy (*Hedera helix*), arnica (*Arnica montana* L), rosemary (*Rosmarinus officinalis* N), of marigold (*Calendula officinalis*), sage (*Salvia officinalis* L), ginseng (*Panax ginseng*), St. John's wort (*Hypericum perforatum*), of butcher's broom (*Ruscus aculeatus* L), meadowsweet (*Filipendula ulmaria* L), orthosiphon (*Orthosiphon stamincus* benth), birch (*Betula alba*), cecropia and argan tree; *Ginkgo biloba*, horsetail, escin, cangzhu, *Chrysanthellum indicum*, Dioscorea plants rich in diosgenin or pure diosgenin or hecogenin and compounds thereof, *Ballota, Guioa, Davallia, Terminalia, Barringtonia, Trema, Antirobia*, bitter orange (*Citrus aurantium*); and an extract of cocoa bean shells (*Theobroma cacao*) such as sold under the name Caobromine® by Solabia. In one embodiment, the personal care composition can include from about 0.0001%, 0.001%, 0.01%, 0.05%, 0.1%, 0.5%, or 1% to about 30%, 25%, 20%, 10%, 7%, 5%, or 3%, by weight of the composition, of one or more anti-cellulite agents.

In one embodiment, the composition can include from about 0.0001%, 0.001%, 0.01%, 0.05%, 0.1%, 0.5%, or 1% to about 30%, 25%, 20%, 10%, 7%, 5%, or 3%, by weight of the composition, of one or more desquamation actives. Examples of desquamation actives include beta-hydroxy acids such as salicylic acid and its derivatives (including 5-(noctanoyl)salicylic acid also known as capryloyl salicylic acid) and alpha-hydroxy acids such as glycolic acid, citric acid, lactic acid, tartaric acid, malic acid or mandelic acid; 8-hexadecene-1,16-dicarboxylic acid or 9-octadecenedioic acid; urea; gentisic acid; oligofucoses; cinnamic acid; *Saphora Japonica* extract; and resveratrol.

Examples of anti-acne actives include resorcinol, sulfur, salicylic acid, retinoids such as retinoic acid and its derivatives, sulfur-containing amino acids and their derivatives and salts (e.g., N-acetyl derivatives such as N-acetyl-L-cysteine), and lipoic acid; benzoyl peroxide, octopirox, tetracycline, 2,4,4' trichloro-2'-hydroxy diphenyl ether, 3,4, 4'-trichlorobanilide, azelaic acid and its derivatives, phenoxyethanol, phenoxypropanol, phenoxyisopropanol, ethyl acetate, clindamycin and meclocycline. In one embodiment, the composition includes from about 0.0001%, 0.001%, 0.01%, 0.05%, 0.1%, 0.5%, or 1% to about 30%, 25%, 20%, 10%, 7%, 5%, or 3%, by weight of the composition, of one or more anti-acne compounds.

In one embodiment, the composition can include from about 0.0001%, 0.001%, 0.01%, 0.05%, 0.1%, 0.5%, or 1% to about 30%, 25%, 20%, 10%, 7%, 5%, or 3%, by weight of the composition, of one or more anti-oxidant/radical scavengers. Examples of anti-oxidants include butylated hydroxytoluene (BHT) and butylated hydroxyanisole (BHA); ascorbic acid (vitamin C), tocopherol (vitamin E), tocopherol sorbate, tocopherol acetate, other esters of tocopherol, 6-hydroxy-2,5,7,8-tetramethylchroman-2-carboxylic acid (commercially available under the tradename Trolox®), amines (e.g., N,N-diethylhydroxylamine, amino-guanidine), nordihydroguaiaretic acid, bioflavonoids, amino acids, silymarin, sorbic acids and its salts, lipoic acid, olive extracts, green tea extracts, white tea extracts, black tea extracts, polyphenols such as proanthocyanidine from pine bark, carotenoids, curcumin compounds such as tetrahydrocurcumin, OCTA (L-2-oxo-4-thiazolidine carboxylic acid), glutathione, and grape skin/seed extracts can be used. Suitable anti-oxidants/radical scavengers can be selected from esters of tocopherol such as tocopherol acetate.

The personal care compositions of the present invention can contain a safe and effective amount of a conditioning agent selected from, for example, humectants, moisturizers, occlusives, and emollients which can be applied to keratinous tissue. In one embodiment, the composition can include from about 0.0001%, 0.001%, 0.01%, 0.05%, 0.1%, 0.5%, or 1% to about 50%, 25%, 20%, 10%, 7%, or 5%, by weight of the composition, of one or more conditioning agents.

Humectants are one group of conditioning agents. Examples of humectants include polyhydric alcohols, water soluble alkoxylated nonionic polymers, and mixtures thereof.

Examples of polyhydric alcohols include glycerin, sorbitol, propylene glycol, butylene glycol, pentylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, hyaluronic acid, sodium adenosine phosphate, sodium lactate, pyrrolidone carbonate, glucosamine, cyclodextrin, and mixtures thereof. Examples of water soluble alkoxylated nonionic polymers include polyethylene glycols and polypropylene glycols having a molecular weight of up to about 1000 such as those with CTFA names PEG-200, PEG-400, PEG-600, PEG-1000, and mixtures thereof.

Examples of conditioning agents include guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyethylene glycols, sugars (e.g., melibiose), cellulose, dextrin, starches, sugar and starch derivatives (e.g., alkoxylated glucose, fucose), lactamide monoethanolamine, acetamide monoethanolamine, panthenol, allantoin, amylose, hyaluronic acid, sodium hyaluronate, betaglucan, glycogen, alguronic acid, galactoarabinan and mixtures thereof; extracts that contain polysaccharides such as TriMoist KMF (Mibelle AG Biochemistry), Fucogel® and Glycofilm® (Solabia Group), Aquaxyl™ (Seppic), Pheohydrane P (Barnet Products Corporation), Aesthigel (Barnet Products Corporation), Pentacare HP (Pentapharm), and Hyalurosmooth (Laboratoires Serobiologiques); $C_1$-$C_{30}$monoesters and polyesters of sugars and related materials.

The personal care composition can include botanical extracts. In one embodiment, the composition includes from about 0.0001%, 0.0005% 0.001%, 0.01%, 0.05%, 0.1%, 0.5%, or 1% to about 30%, 25%, 20%, 10%, 7%, 5%, or 3%, by weight of the composition, of one or more botanical extracts. Examples of botanical extracts include extracts from plants (herbs, roots, flowers, fruits, seeds) such as flowers, fruits, vegetables, and so on, including yeast ferment extract, *Padina pavonica* extract, thermus thermophilis ferment extract, *Camelina sativa* seed oil, boswellia serrata extract, olive extract, *Bodopsis thaliana* extract, *Acacia dealbata* extract, *Acer saccharinum* (sugar maple), acidopholus, acorns, aesculus, Alicaligenes polysaccharides, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and the like. Further specific examples include, but are not limited to, *Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officianalis*, Citrus *Medica limonum, Ginkgo biloba* Panax Ginseng, *Siegesbeckia orientalis, Fructus mume, Ascophyllum nodosum, Bifida ferment* lysate, *Glycine soja* extract, Beta Vulgaris, *Haberlea rhodopensis, Polygonum cuspidatum*, Citrus *Aurantium dulcis, Vitis vinifera, Selaginella tamariscina, Humulus lupulus*, Citrus *Reticulata peel, Punica granatum, Asparagopsis, Curcuma longa, Menyanthes tri-*

*foliata, Helianthus annuus, Hordeum vulgare, Cucumis sativus, Evernia prunastri, Evernia furfuracea, Laminaria angustata, Laminaria cloustoni, Laminaria digitata, Laminaria digitata, Laminaria hyperborea, Laminaria japonica, Laminaria longissima, Laminaria ochotensis, Laminaria ochroleuca, Laminaria saccharina*, and mixtures thereof. Other suitable actives are listed in the functional category of "Biological Products" in the Personal Care Product Council's *International Cosmetic Ingredient Dictionary and Handbook*, Thirteenth Edition, 2010.

In one embodiment, the composition includes from about 0.0001%, 0.001%, 0.01%, 0.05%, 0.1%, 0.5%, or 1% to about 10%, 7%, 5%, 2%, or 1%, by weight of the composition, of one or more preservatives. Examples of preservatives include benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, sodium benzoate, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM hydantoin, DEDM hydantoin dilaurate, dehydroacetic acid, diazolidinyl urea, dibromopropamidine diisethionate, DMDM hydantoin, glyceryl caprylate, potassium sorbate, salicylic acid, hexamidine, capryloyl glycine, 1,2 hexanediol, undecylenoyl glycine, ethylhexylglycerin, caprylhydroxamic acid, methylpropanediol, hinokitiol, sodium hinokitiol, phenylethyl alcohol, levulinec acid, p-anisic acid, 2-bromo-2-nitropropane-1,3-diol, sodium hydroxymethylglycinate, iodopropynyl butyl carb amate, methylchloroisothiazolinone, methylisothiazolinone, piroctone olamine, cinnamon oil, rosemary extract, Biopein® (available form Bio-Botanica), Naticide® (available form Sinerga), and combinations thereof In one embodiment, the composition is free of parabens and/or formaldehydes.

Depending upon the form and function, the personal care composition can include one or more detersive surfactants. If and when present, the detersive surfactant component can be included to provide cleaning performance to the composition. The detersive surfactant component in turn can comprise anionic detersive surfactant, zwitterionic or amphoteric detersive surfactant, or a combination thereof.

The composition can include from about 1%, 2.5%, 5%, 7.5%, 10%, 12.5%, or 15% to about 50%, 40%, 30%, 25%, 20%, or 10%, by weight of the detersive surfactants in the composition. Examples of anionic detersive surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Examples of amphoteric detersive surfactants include cocoamphoacetate, cocoamphodiacetate, lauroamphoacetate, lauroamphodiacetate, and mixtures thereof. Examples of other anionic, zwitterionic, amphoteric or optional additional surfactants are described in McCutcheon's, *Emulsifiers and Detergents,* 2010 Annual Ed., published by M. C. Publishing Co., and U.S. Pat. Nos. 3,929,678, 2,658,072, 2,438,091, and 2,528,378.

Emollient Compositions Including Alkenones or Alkenone-Derived Compounds

Dermatitis is a general term describing inflammation of the skin. It can have many causes and occurs in many forms, but usually involves an itchy rash and/or swollen, reddened skin. In the U.S., approximately 31.6 million people are afflicted with some form of dermatitis. Emollients are agents used to treat dermatitis, which generally come in the form of creams, ointments, or lotions. They help skin feel more comfortable by maintaining skin moisture and flexibility thereby preventing painful cracking and other irritations. When used regularly, emollients can be used to treat mild to moderate eczema. See, e.g., "Emollients," National Eczema Society, www.eczema.org/emollients.

Even for those not suffering from eczema/atopic dermatitis, various daily-use emollient formulations are available to combat general skin irritation. Repeated skin cleansing, while an important component of overall well-being and personal health, is very drying to the skin. In addition to removing dirt, sebum residues, and microorganisms, cleansing can also remove or disrupt essential skin oils resulting in dryness and irritation. Post-cleansing emollient-containing creams, lotions, shower gels, etc., can restore and maintain skin health.

Aside from being used to treat skin ailments, emollients are also common to a number of skin-care, hair-care, and cosmetic products to improve sensorial properties both during application and final after-feel. An emollient's chemical nature and associated physical properties such as spreading attributes, viscosity, and lubricity each contribute to its performance in formulation. The structures of algal polyunsaturated long-chain alkenones and alkenone derivatives of the present disclosure are uniquely suited to serve as emollients, compared to existing emollients based on waxes and oils from petroleum (e.g., paraffin wax, petroleum jelly, mineral oil, etc.), silicones, or fatty acids, which can pose certain environmental and potential toxicity hazards. See, e.g., European Centre for Ecotoxicology and Toxicology of Chemical, Linear Polydimethylsiloxanes (viscosity 10-100, 000 centistokes), ECETOC Joint Assessment of Commodity Chemicals No. 26., September 1994.

Figure 2:
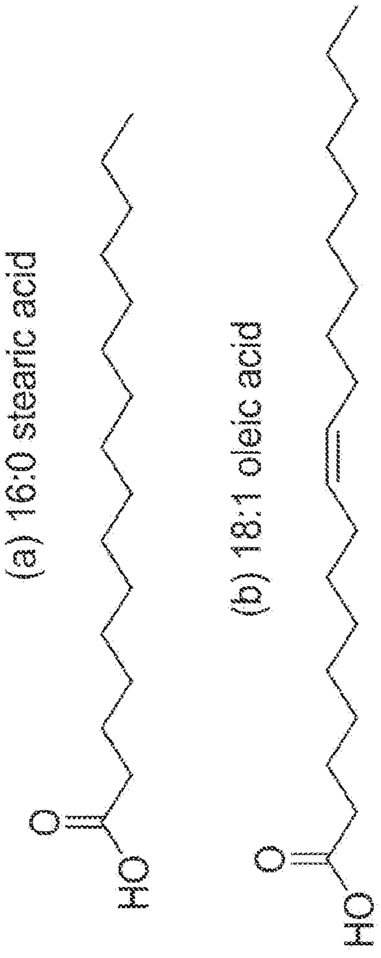
FIG. 2 shows the structure of an embodiment of saturated fatty acids, specifically stearic acid from animal fat; and the structure of an embodiment of unsaturated fatty acid, specifically oleic acid from olive oil. Fatty acid nomenclature is given as number of carbons:number of cis-double bonds. Without wishing to be bound by theory, it is believed that the incorporation of a cis-alkene into a fatty acid structure provides a compound that is a less ideal emollient by increasing fluidity and decreasing (oxidative) stability.
Figure 3:
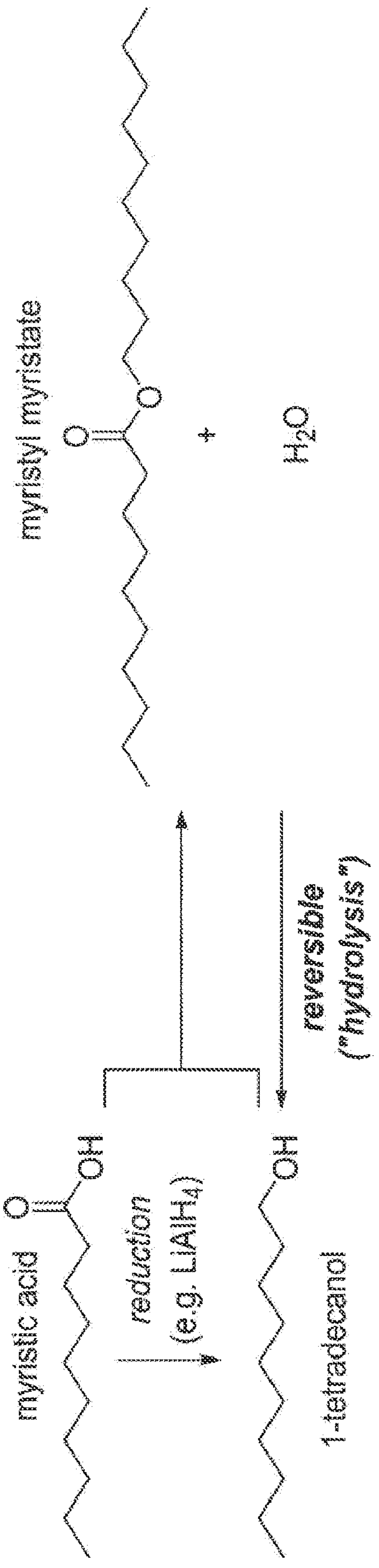
FIG. 3 is a scheme of a representative synthesis of a cetyl ester, myristyl myristate, made by reversible condensation of myristic acid with tetradecanol. Tetradecanol is itself a reduction product of myristic acid, and can be made under harsh reaction conditions (e.g., lithium aluminum hydride, $LiAlH_4$).

For fatty-acid emollients, saturated fats like stearic acid from animal fat are superior to unsaturated fats common to most plants (e.g., oleic acid in olive oil, FIG. 2). Saturated fats exhibit preferred physical properties such as higher melting points and viscosities, along with enhanced chemical (i.e., oxidative) stabilities. Examples of the structure and nomenclature of fatty acids are shown in FIG. 2. However, animal-based products have generally fallen out of favor with the trend toward more sustainable vegetable-based materials, evidenced by the growing vegan movement. See, e.g., Cherry, E. "Veganism as a Cultural Movement: A Relational Approach," *Social Movement Stud.* 2006, 5, 155-170). Referring to FIG. 3, one example of plant-based saturated fatty acid emollients is cetyl esters. These are made from a combination of a saturated fatty acid and fatty alcohol with the resulting waxy esters (m.p. ~40-60° C.) often used to provide desired properties to creams and lotions such as thickening, fatting, emulsion enhancing and opacifying effects to various personal care products. For example, referring to FIG. 3, myristal myri state is made by condensing myristic acid, the primary component of nutmeg oil, with tetradecanol. The synthesis of fatty alcohols like tetradecanol is however non-trivial, because reduction of the corresponding fatty acid (e.g., myristic acid for tetradecanol and palmitic acid for cetyl alcohol) can require high temperatures/pressures, moisture-free and/or inert gas atmospheres, and can liberate explosive hydrogen gas. Additionally, the condensation reaction between the fatty acid and alcohol is reversible, making cetyl esters potentially hydrolytically unstable.

Accordingly, in one aspect, compositions containing the compounds of the present disclosure are creams, ointments, or lotions. In some embodiments, the compositions include an alkenone or alkenone derivative of the present disclosure, oil (e.g., an acylglycerol), and/or a fatty acid.

Figure 4:
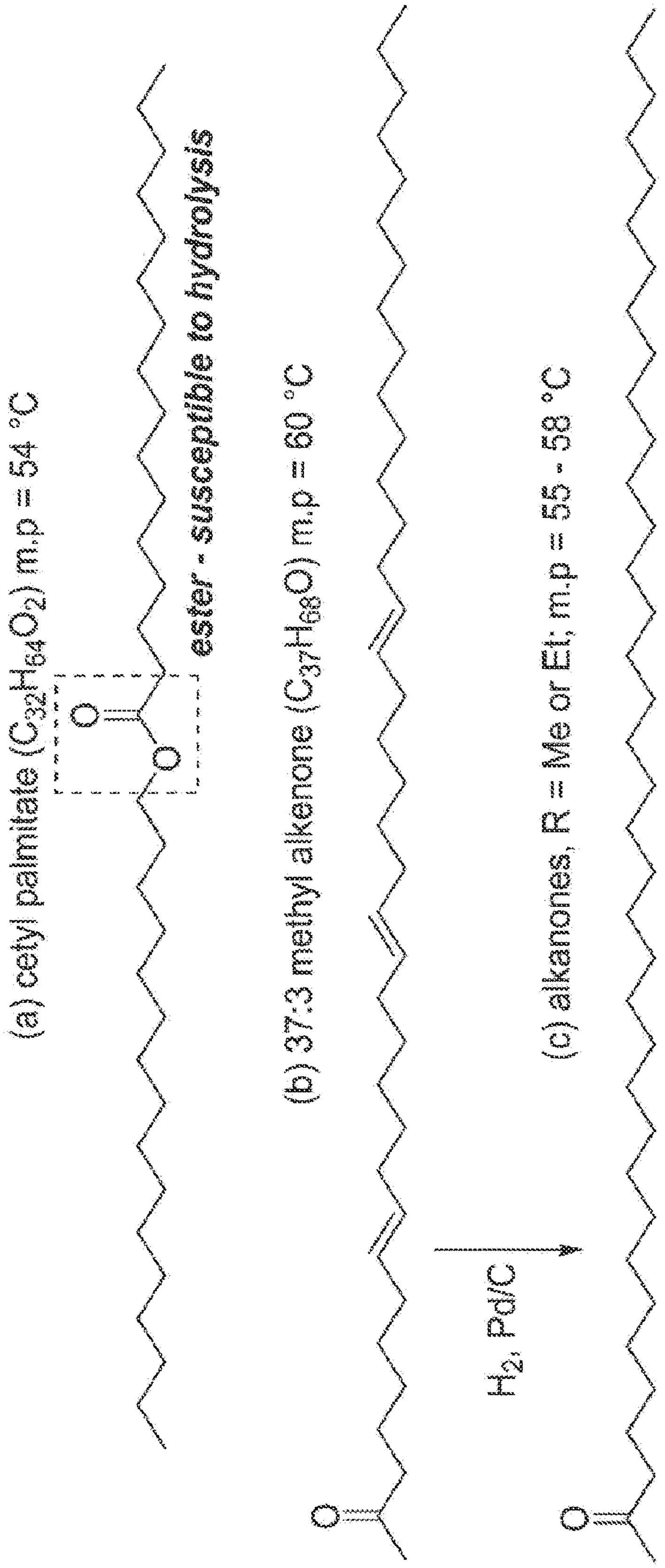
FIG. 4 is a comparison of 37:3 methyl alkenone to the corresponding hydrogenated alkanone and to cetyl palmitate, a fatty emollient. While the molecular formulas and melting points are similar, alkenones and alkanones are not prone to hydrolysis because they lack an ester linkage.

By virtue of their long-chain length, alkenones possess the appropriate physical properties for use as emollients, and can be used in some embodiments without further manipulation (i.e., waxy solids at room temperature (m.p.=60-70° C.), with similar properties to cetyl esters). They contain chemically stable trans-double bonds compared to the cis-methylene interrupted alkenes that are responsible for the poor oxidative stability of vegetable-derived fats. Moreover, hydrogenation of the double bonds in the alkenones provides saturated alkenones ("alkanones") with slightly lower melting points closer to cetyl esters (FIG. 4). Because both alkenones and alkenones do not contain an ester functional group but rather a ketone, they are thus not prone to hydrolysis. Alkenones are advantageously biodegraded by aerobic bacteria (see, e.g., Zabeti, N. et al. FEMS Microbiol . Ecol., "Potential alteration of $U^{K}_{37}$ paleothermometer due to selective degradation of alkenones by marine bacteria isolated from the haptophyte *Emiliania huxleyi," FEAIS Microbiol. Ecol.,* 2010, 73, 83-94), thereby allowing these compounds and alkenone derivatives to conform to EPA environmental safety standards. See, e.g., Environmental Protection Agency: Safer Choice Standard and Criteria, http://www2.epa.gov/saferchoice/standard (accessed Nov. 2, 2015).

Others skin-care compositions including alkenone and alkenone derivatives can improve, restore, and/or maintain skin health, by providing a moisture barrier as emollients or occlusive agents. Additionally, these compositions can have cosmetic applications such as creating a desirable waxy sheen in coloring agents (e.g., lipsticks), hair, or other personal products.

In one embodiment, one or more alkenones or alkenone derivatives of the present disclosure are present from 1-50% w/w of the total composition. Products made directly from algal oil (approximately 10% w/w alkenones) are typically on the low range of total alkenone content after formulation. Higher percentage alkenone-containing products outlined in Table 1 below can be achieved by incorporating purified alkenones to perform specific functions in personal care products.

TABLE 1

Alkenone percentage in personal care compositions based on role of alkenone.

| Alkenone Role in Composition | Preferred Alkenone Content (w/w %) |
|---|---|
| Abrasive | 5-15 |
| Wax | 5-15 |
| Emollient | 10-35 |
| Surfactant | 10-35 |

As an example, an emollient composition can include one or more acylglycerols, one or more fatty acids; and one or more alkenones. In some embodiments, the one or more acylglycerols, one or more fatty acids, and the one or more alkenones can each independently be present in an amount of from 2% (e.g., from 5%, from 8%, or from 10%) to 15% (e.g., to 10%, to 8%, or to 5%) by weight in the emollient composition.

As another example, an alkenone-containing emollient composition can contain one or more alkenones, one or more oils (e.g., mono-, di-, and triglycerides), one or more alcohols (e.g., glycerin or fatty alcohols), and water. In some embodiments, the one or more alkenones, one or more oils (e.g., mono-, di-, and triglycerides), and one or more alcohols can each independently be present in an amount of from 2% (e.g., from 5%, from 8%, or from 10%) to 15% (e.g., to 10%, to 8%, or to 5%) by weight in the emollient composition. In some embodiments, the emollient composition include from 50% (e.g., from 60%, or from 70%) to 80% (e.g., to 70%, or to 60%) by weight of water. As used herein, it is understood that where percentage ranges (e.g., weight percent or volume percent) for components of a composition are provided, the sum of the percentages of all the components for a specific composition does not exceed 100%. For example, the sum of the percentages of all the components for a specific composition is 100%.

Cleanser Compositions Including One or More Alkenone or Alkenone-Derived Exfoliant and One or More Surfactant The accumulation of dead skin cells on the outermost layer of the skin can cause not only undesirable appearance (e.g., dry, dull and flaky), but can also lead to certain skin conditions such as acne. Exfoliation is a process by which the outermost, oldest dead skin cells are removed. Not only does this increase skin softness and appearance, but is also important for maintaining skin health by encouraging proper cell turnover.

Two types of exfoliants exist: mechanical exfoliants and chemical exfoliants. Chemical exfoliation (e.g., "chemical peels") is believed to stimulate new skin cell growth and/or promote dead skin cell loss through interactions of the exfoliant compound with certain proteins. See, e.g., Coleman, W.P.; Brody H.J., "Advances in chemical peeling," *Dermatol. Clin.* 1997, 15, 19-26. Chemical exfoliation has been reported for treatment of serious skin conditions linked to photodamage such as actinic keratosis and other cancers. See, e.g., Rendon, M.I.; Berson, D. S.; Cohen, J.L.; Roberts, W.E.; Starker, I.; Wang, B., "Evidence and considerations in the application of chemical peels in skin disorders and aesthetic resurfacing," *J. Clin. Aesthet. Dematol.* 2010, 3, 32-43. These deep exfoliations are specialized treatments with associated recovery protocols.

Mechanical exfoliation involves the use of abrasives to remove dead skin cells on the outermost layer of the skin. This type of exfoliation is more commonplace with mechanical exfoliating agents found in a variety of daily-use cleansers. Historically abrasive exfoliants were made from polyethylene, and their widespread and prolonged use has led to an accumulation and persistence of these materials. The environmental implications of the large amount of microplastics, particularly in the marine environment, are only recently becoming appreciated, as evidenced by a series of recent reports. See, e.g., Napper, I.E.; B akir, A.; Rowland, S.J.; Thompson, R C., *Marine. Poll. Bull.* 2015, 99, pp. 178-185, DOI: 10.1016/j.marpolbul.2015.07.029. Eco-friendly exfoliating agents include ground nut shells and fruit pits. However, these materials fail to match the smoothness of polyethylene beads resulting in increased skin irritation.

Alkenones and alkenone derivatives (e.g., alkenones) of the present disclosure are waxy solids at room temperature (melting points ~60-70° C.) with limited solubility in compositions that include surfactants (e.g., soaps). They would therefore exist as solids in surfactant-containing compositions and could serve as gentle mechanical exfoliants in various cleansers. In some embodiments, alkenone waxes within these compositions can form films during cleansing, for instance as they melt when used with warm water followed by cooling. Formation of these waxy films can minimize surfactant skin penetration and the resultant resulting irritation, ideal for sensitive skin products. The films can also provide desirable sheen to, for instance, compositions for conditioning hair.

In one embodiment, the composition includes one or more surfactants (e.g., fatty acid carboxylate, sulfates, or betaines); and one or more alkenones and/or alkenone derived compounds of the present disclosure (e.g., alkenones).

The composition can include (exfoliating) skin cleansers or conditioners (e.g., hair). By replacing microplastic abrasives with alkenones, the composition could be made from natural components or biodegradable components with significantly reduced environmental impact. Alkenones and/or alkenone derivatives in these mixtures can also help mitigate irritation and/or provide desirable aesthetic qualities. Using the oils and soaps from algae along with the alkenones and/or alkenone-derived compounds represents a substantive departure from traditional agricultural plant-based formulations toward more sustainable personal care compositions.

In some embodiments, an example of an alkenone-containing cleansing composition includes one or more alkenones and/or alkenone-derived compounds of the present disclosure, one or more oils (e.g., mono-, di-, and triglycerides), one or more fatty surfactants (e.g., sodium laureth sulfate, cocamidopropyl betaine), one or more alcohols (e.g., glycerol or fatty alcohols), and water. In some embodiments, the one or more alkenones and/or alkenone-derived compounds of the present disclosure, one or more oils (e.g., mono-, di-, and triglycerides), one or more fatty surfactants (e.g., sodium laureth sulfate, cocamidopropyl betaine), and one or more alcohols (e.g., glycerol or fatty alcohols) are each independently present in an amount of from 2% (e.g., from 5%, from 10%, from 15%, or from 20%) to 25% (e.g., to 20%, to 15%, to 10%, or to 5%) by weight in the cleansing composition. In some embodiments, the cleansing composition include from 50% (e.g., from 60%, or from 70%) to 80% (e.g., to 70%, or to 60%) by weight of water.

Compositions Including One or More Alkenone-Derived Emulsifier/Surfactant

Emulsifiers are defined as compounds used to stabilize emulsions, or dispersions of two immiscible substances. Many emulsion-based cosmetics and personal care products contain emulsifiers to achieve desired textural properties and increase product lifetime. Emulsifiers have also been used as delivery vehicles or encapsulating agents to improve the absorption profiles and bioavailablity of various active agents. See, e.g., Souto, E.B.; Severino, P.; Basso, R.; Santana, M.H.A., "Encapsulation of Antioxidants in Gastrointestinal-Resistant Nanoparticulate Carriers," *Oxidative Stress and Nanotechnology: Methods and Protocols* (D. Armstrong and D.J. Bharali, eds.), Springer Science, New York, 2013. The structures of emulsifiers are characterized as containing both hydrophilic and hydrophobic (lipophilic) components.

Figure 5:
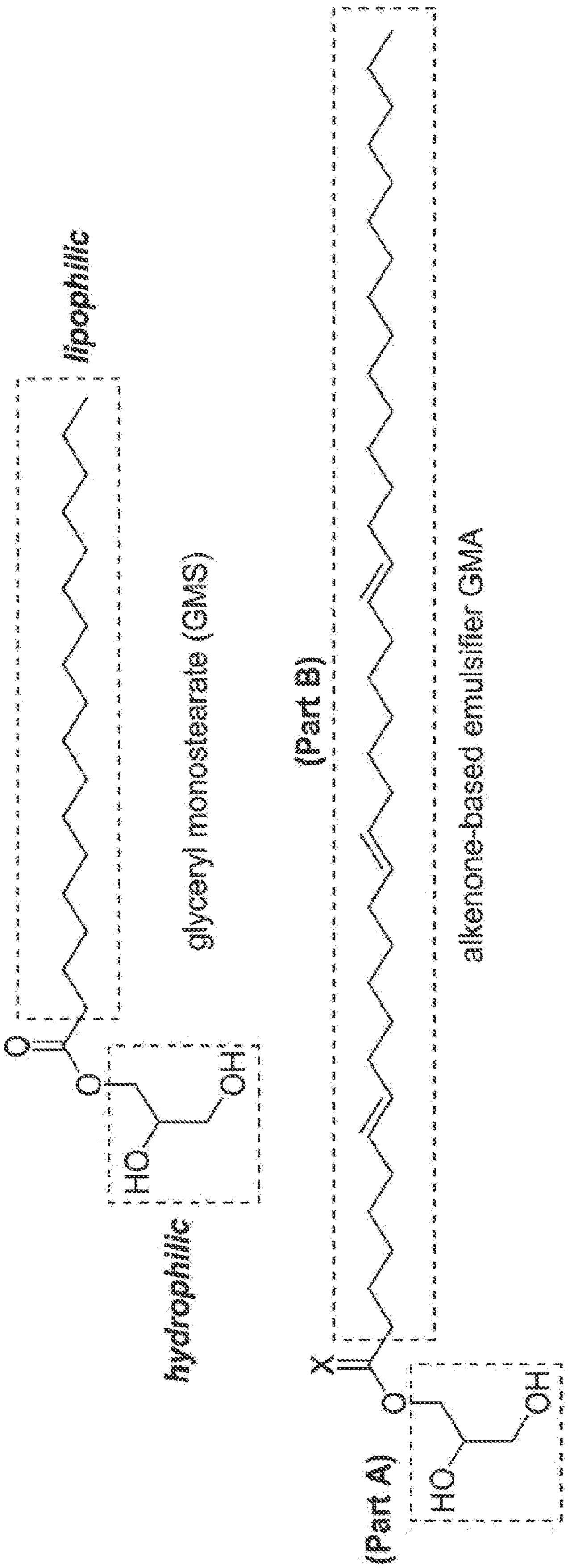
FIG. 5 is a comparison of a fatty-acid based emulsifier, glyceryl monostearate (GMS), and an alkenone-derived emulsifier glyceryl monoalkenone ("GMA"). The properties of an emulsifier are dependent on the so-called hydrophilic-lipophilic balance (HLB), i.e., the relative sizes of the hydrophilic and lipophilic portions of the molecule. The HLB value of monoacylated alkenone glyceryl emulsifiers such as GMA is different than GMS and other fatty acid emulsifiers and provides superior performance. Stearic acid, used to make GMS, is an animal product.

Historically, emulsifier technology was based on petrochemicals such as ethylene glycol or mineral oils. For environmental reasons, there has been a shift toward renewable feedstocks. One example is fatty acid (poly)glycerol esters. Glycerol monostearate (GMS) typifies this class of waxy fatty acid emulsifiers, composed of a hydrophilic glycerol component and hydrophobic stearic acid chain (FIG. 5). The physical properties and performance of emulsifiers are directly related to the balance between its hydrophobic and lipophilic groups (HLB value). In the case of (poly)glyceryl fatty esters, this would be controlled by the fatty acid carbon chain length and structure (i.e., unsaturation profile) along with the degree of (poly)glycerol acylation (e.g., mono-, di-, or triglycerides). However, the choice of fatty acid and amounts used in these systems can be constrained by source considerations for a particular fatty acid. For instance, if the fatty acid is from an animal product or a resource intensive (e.g., land and water) edible agricultural crop.

Incorporation of alkenones, with carbon chain lengths approximately twice as long as fatty acids and trans- vs. cis-double bonds, into a glycerol backbone (e.g., a glyceryl monoalkenone (GMA) as shown in FIG. 5) can provide lipophilic emulsifiers with unique properties ideally suited for certain applications. Additionally, compounds from microalgae can decrease controversies associated with the use of fatty acids from other feedstocks. It is believed that these alkenone-derived emulsifiers do not occur in nature.

Most emulsifiers can be considered surfactants, compounds that lower the surface tension between two immiscible liquids or between a liquid and solid. It is believed that the degree to which an emulsifier is surface-active is controlled by the HLB. Due to their unique structure, alkenone-derived surfactants would be expected to exhibit different HLB values and thus novel properties when compared to current fatty acid based technologies. Specifically, alkenone surfactants have lower (i.e., more lipophilic) HLB values than their fatty acid counterpart. This is important because for a given formulation, HLB values of the different ingredients (e.g., components A, B and C) are additive:

$$HLB_{mix}=xHLB_A+yHLB_B+(1-x-y)HLB_C.$$

Because different compositions can have different specified HLB mi x ranges, the incorporation of an alkenone-based surfactant into these blends can therefore provide a new means for achieving the requisite HLB values for these products. Individual alkenone HLB values can also be tuned through the incorporation of neutral-(lower HLB) or ionic-head groups (higher HLB). The lipophilic portion can also be manipulated to differing carbon chain lengths as outlined in the '460 Application.

Aside from HLB, alkenone-based surfactants can also lend other desirable and superior properties to compositions that include the alkenone-based surfactants. For example, skin irritation from cleansing with surfactants can be caused by the removal of free fatty acids and fatty acid glycerides leading to changes in the intercellular lipid profile. See, e.g., Denda, M.; Koyama, J.; Namba, R. Horii, I., "Stratum corneum lipid morphology and transepidermal water loss in normal skin and surfactant-induced scaly skin," *Arch. Dermatol. Res.* 1994, 286, 41. Moreover, surfactants can penetrate the stratum corneum where they are adsorbed onto proteins (e.g., keratin) and can mix with intracellular lipids. The long hydrocarbon chain of alkenone-based surfactants and dissimilarity with native skin lipids can minimize solubilization (i.e., fatty acid removal), mixing, and skin penetration of these compounds. Ananthapadmanabhan, K.P.; Moore, D.J.; Subramanyan, K.; Misra, M.; Meyer, F., "Cleansing without compromise: the impact of cleansers on the skin barrier and the technology of mild cleansing," *Dermatologic Ther.* 2004, 17(s1), 16-25. Aside from improved cleansing performance, alkenone-based surfactants can also lend desirable aesthetic properties such as a desired foaming behavior.

The structures of synthetic alkenone-derived surfactants includes a polar headgroup ("Part A") and hydrophobic tail ("Part B", FIG. 5) wherein any group in Part A can be an: alcohol, ester, acid, carboxylate, sulfonate, phosphonate, ammonium or any combinations thereof. Part B is comprised of an alkenone hydrocarbon chain (35-40 carbons, 1-4 trans-double bonds). The dual nature (hydrophobic/hydrophilic) of these derivatives would also make possible their use as delivery systems for encapsulating active agents (e.g., antioxidants). Recalcitrance of alkenones to degradation (see, e.g., Brassell S.C. (1993), "Applications of biomarkers for delineating marine paleoclimatic fluctuations during the Pleistocene," in Organic Geochemistry (M.H. Engel and S.A. Macko, eds.), pp. 699-738, Plenum Press, New York) might permit slow release of these active agents thereby increasing product lifetime in comparison to other traditional fatty acid-based encapsulation methods. See, e.g., Takahashi, M.; Kitamoto, D.; Asikin, Y.; Takara, K.; Wada, K., "Liposomes Encapsulating Aloe vera Leaf Gel Extract Significantly Enhance Proliferation and Collagen Synthesis in Human Skin Cell Lines," *J. Oleo. Sci.* 2009, 58, 643-650.

Figure 6:
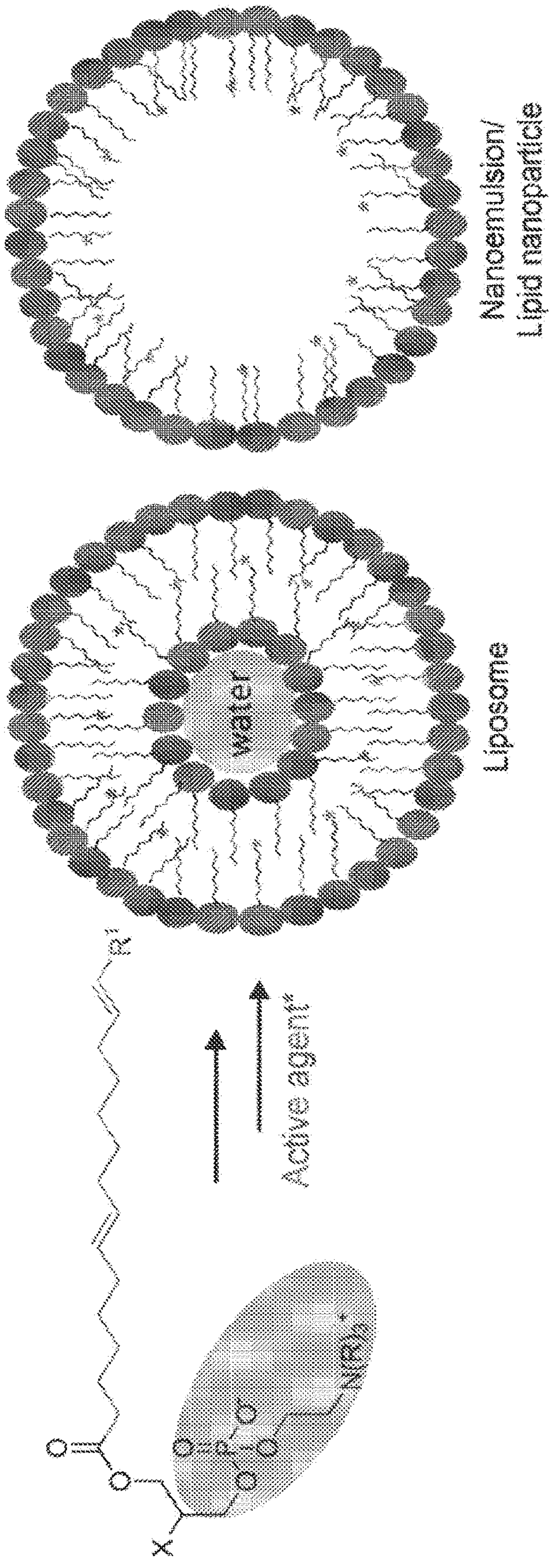
FIG. 6 is an illustration of an embodiment of an alkenone-based choline phosphate encapsulation system to improve active agent (*) delivery. The longer hydrocarbon chain length of alkenones compared to fatty acids (see, e.g., FIGS. 1A and 1B) that have traditionally been used for encapsulation methods can provide unique secondary and tertiary structures (e.g., liposomes and micelles with elongated hydrophobic regions).

FIG. 6 shows an alkenone-based choline phosphate encapsulation system to enhance active agent (*) delivery. The longer hydrocarbon chain length and trans-double bonds of alkenones can provide access to novel secondary and tertiary structures.

In one embodiment, the encapsulating and/or surfactant composition includes one or more alkenone-derived surfactant, one or more mono-, di-, or triglyceride, and one or more alcohol (e.g., glycerol, or fatty alcohol). In some embodiments, one or more alkenone-derived surfactant, one or more mono-, di-, or triglyceride, and one or more alcohol (e.g., glycerol, or fatty alcohol)can each independently be present in an amount of from 2% (e.g., from 5%, from 8%, or from 10%) to 15% (e.g., to 10%, to 8%, or to 5%) by weight in the emollient composition.

The composition can be a soap, a detergent, or a skin cleanser. Alkenone-derived surfactants can be used in mild cleansers (e.g., for infant care) to decrease skin penetration and irritation, as well as encapsulating active agents for controlled release and to increase bioavailability/stability. Cosmetics with certain textural requirements can also benefit from alkenone emulsifiers and/or surfactants.

Isolation and Synthesis of Alkenones and Alkenone Derivatives

Isolation of Alkenones from Algae

The extraction and/or isolation of alkenones and fatty acids from algal biomass and their conversion to jet fuel range hydrocarbons and biodiesel, respectively, has previously been described in the '460 Application, the disclosure of which is hereby incorporated by reference in its entirety, along with any publications, patents, or patent applications cited therein. For example, the term "substantially pure" as used herein refers to a chemical that is chemically pure or analytically pure—the chemical has a purity greater than 70%, greater than 75%, greater than 80%, greater than 85%, greater than 90%, greater than 95%, greater than 8%, or greater than 99%. In the present disclosure, different compound sub-classes can be separated to create pools of pure isolates as outlined in the '460 Application from which optimized personal care formulations can be created. Additionally, pigments can be selectively removed from lipid mixtures to create decolorized compositions with colors that are better suited to personal care items such as soaps and creams.

Figure 7:
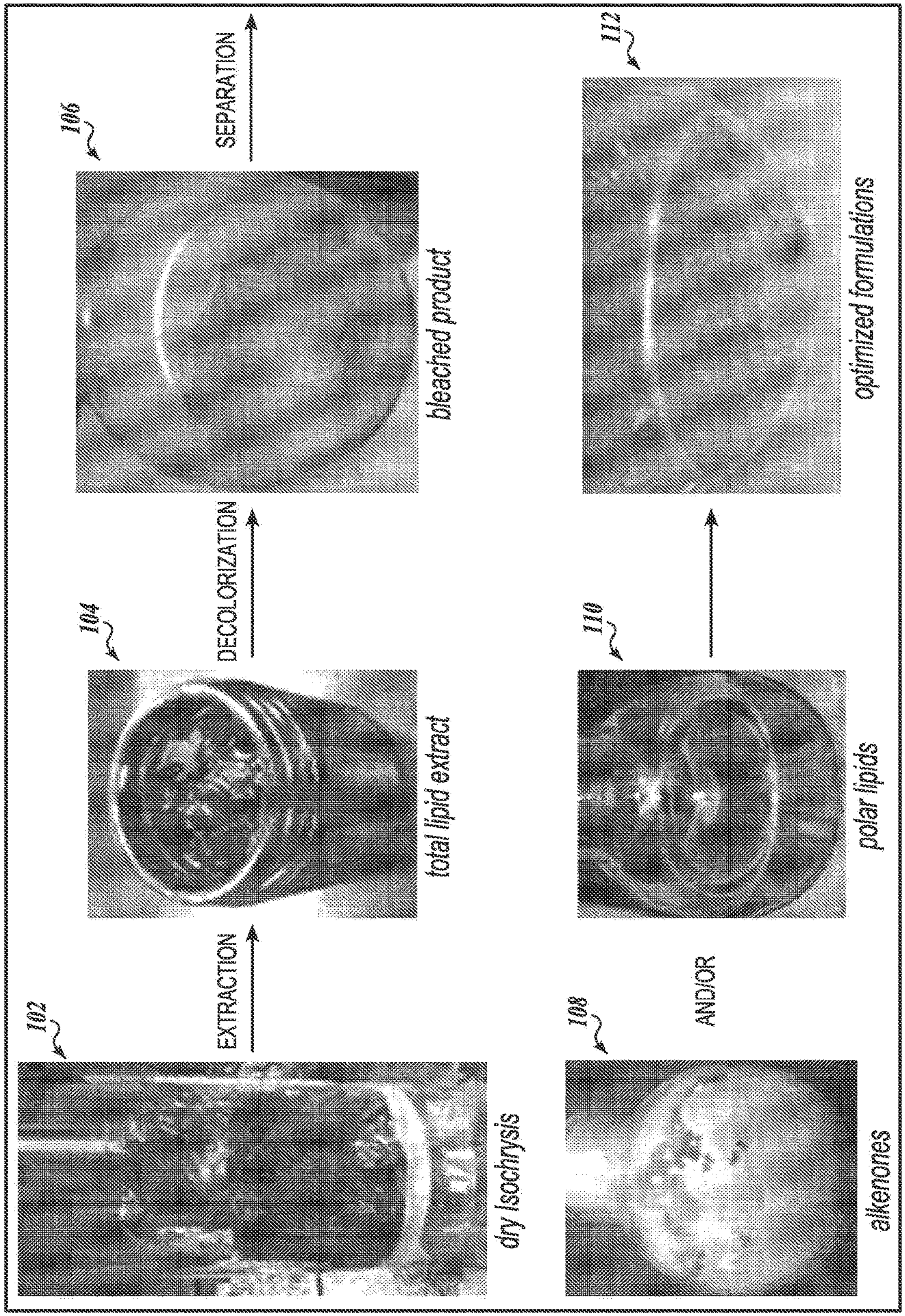
FIG. 7 is an embodiment of an extraction sequence of alkenones from algae.

FIG. 7 shows the extraction, processing, separation, and formulation of alkenone-based topical products from *Isochrysis* biomass. Dry *Isochrysis* biomass 102 is first extracted (e.g., with an organic solvent) to provide a dark colored alkenone-containing (e.g., around 15% w/w) total lipid extract 104. Green naturally abrasive surfactants can be directly formed from this product by saponification of acylglycerols along with lighter colored products by removal of pigments (i.e., decolorization) as shown in product 106. Alternatively, purified alkenones 108 can be separated from polar lipids 110, fatty acids, glycerides, or soaps), derivatized, and reconstituted to specific compositions for optimized performance 112.

Alkenone Derivatization

Figure 8:
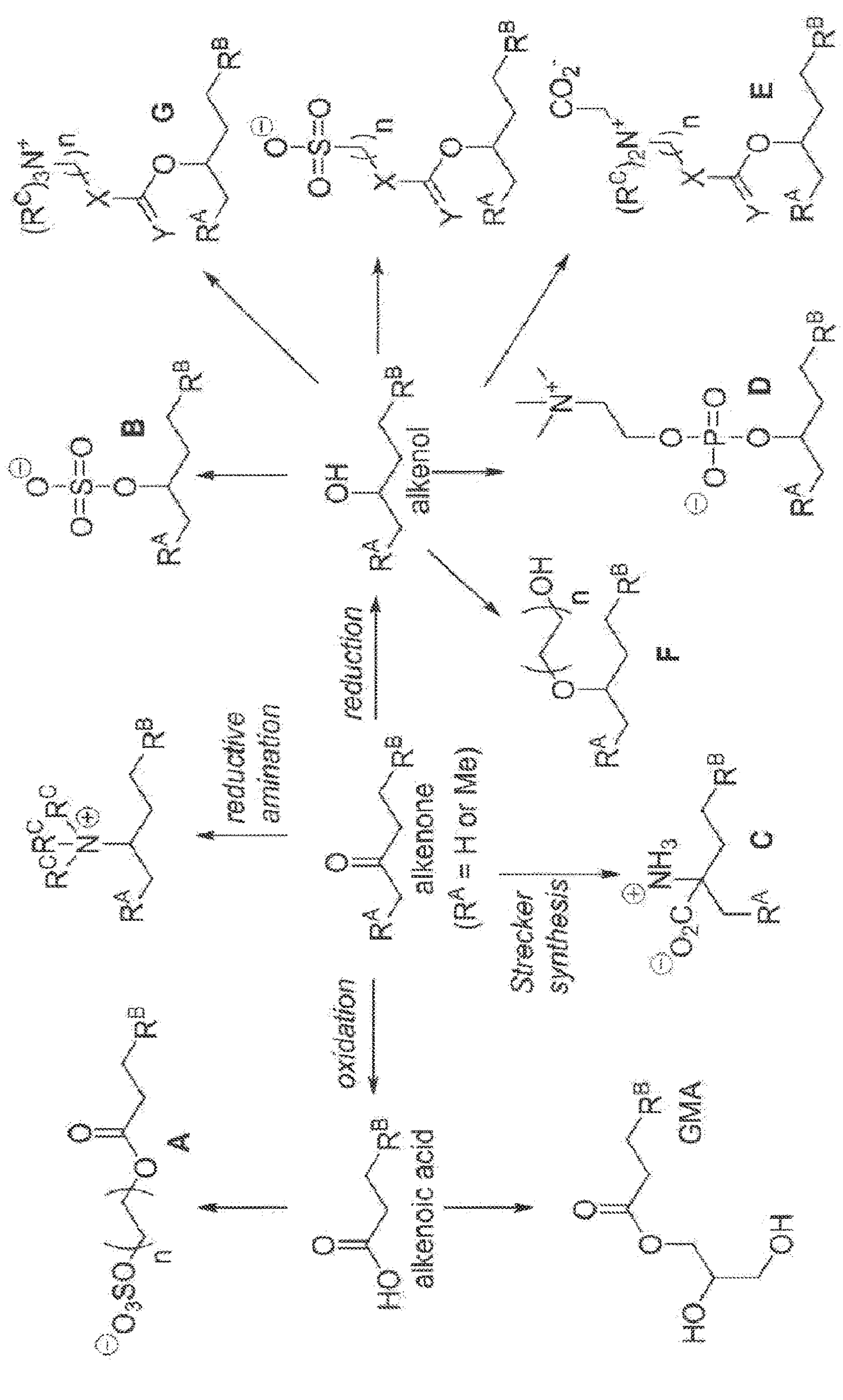
FIG. 8 is a schematic representation of exemplary pathways for converting alkenones to surface active agents where: $R^A$ is H or methyl and $R^C$ is an alkyl group ($C_nH_{2n+1}$, e.g., $CH_3$). X is NH and Y is O. When derived from an alkenone of the present disclosure, $R^B$ can be a $C_{32-37}$ hydrocarbon chain containing one or more trans carbon-carbon double bonds. For example, $R^B$ is $C_{33}$ for an alkenone having 37 total carbons and $R^A$ is H; $R^B$ is $C_{34}$ for an alkenone having 38 total carbons and $R^A$ is H; and $R^B$ is $C_{33}$ for an alkenone having 38 total carbons and $R^A$ is methyl. As described in U.S. application Ser. No. 14/599,460 ("the '460 Application"), this $R^B$ hydrocarbon chain can be modified to $R^B \geq C_5$ alkene (generally containing one alkene) or $C_5$ alkyl.

Examples of synthetic alkenone-derived surfactants are outlined in FIG. 8. One series is based on the use of reduced alkenones ("alkenols") to prepare polyoxyethylene derivatives of the alkenones (F), sulfate derivatives of the alkenones (B), ammonium derivatives of the alkenones (H), and betaine (D, E) surface active agents. Others are derived from oxidized alkenones (alkenoic acids) that would include neutral glyceryl emulsifiers. Amino acid derivatives (C) by Strecker synthesis (see, e.g., A. Baeza, C. Nájera, J.M. Sansano, *Synthesis,* 2007, 1230-1234) can exhibit antimicrobial activities. Referring to FIG. 8, $R^A$ is methyl or ethyl and $R^C$ is an alkyl group ($C_nH_{2n+1}$, e.g., $CH_3$). When derived from an alkenone of the present disclosure, $R^B$ can be a $C_{32}$-$C_{37}$ hydrocarbon chain containing one or more trans-double. As described in the '460 Application, this $R^B$ hydrocarbon chain can be modified to $R^B \geq C_5$ alkene (generally containing one alkene) or $C_5$ alkyl.

Hydrogenation of Alkenones to Alkanones

Alkenones can be hydrogenated to provide alkanones by placing the alkenones under an atmosphere of hydrogen in the presence of a catalyst, such as platinum and/or palladium on carbon. To a solution of alkenones in ethyl acetate was added palladium on carbon (10% wt Pd, 10% w/w alkenones) and the mixture was placed under an atmosphere of hydrogen (1 atm.). The reaction was stirred for 6 h before removing the palladium by filtration through cotton and concentrating the solution in vacuo. The resulting alkanones were obtained as an off-white solid (98% yield, mp.=55-58° C.).

Reduction of Alkenones to Alkenols

Alkenones can be reduced to the corresponding alkenols by any number of standard ketone reduction methods. See, e.g., *Modern Reduction Methods* (P.G. Andersson, I.J. Munslow, eds.), Wiley-VCH, Weinheim, Germany, 2008. The methods generally employ a hydride source ([M]H, where [M] can be Al, B, Si; e.g., $LiAlH_4$ or $NaBH_4$) or the combination of hydrogen and a heterogeneous catalyst (e.g., Pd, Pt, Ni). In a standard reaction, alkenones are dissolved in a mixture of an alcoholic solvent (ROH) and ethereal solvent (e.g., tetrahydrofuran) to which is added sodium borohydride ($NaBH_4$) and the mixture is stirred for 1 h. The reaction is then quenched with saturated aq. Brine, and extracted with an organic solvent (e.g., ethyl acetate, diethyl ether). The organic phase is concentrated in vacuo to yield the alkenol products that can be used without further purification (yields are generally>90%).

Oxidation of Alkenones to Alkenoic Acids

The oxidation of alkenones to their corresponding carboxylic acids (alkenoic acids) can be accomplished by a variety of classic methods including the haloform reaction (see, e.g., Fuson, R.C.; Bull, B.A., "The Haloform Reaction," Chem. Rev. 1934, 15, 275-309), Rub ottom oxidation followed by oxidation cleavage (see, e.g., Meinke, P. T.; Colletti, S .L.; Ayer, M.B.; Darkin-Rattray, S.J.; Myers, R.W.; Schmatz, D.M.; Wyvratt, M.J.; Fisher, M.H., *Tetrahedron Lett.* 2000, 41, 7831-7835), or the use of carbon monoxide and water. See, e.g., Larson, A.T., 1942, "Organic Acids from Ketones," and U.S. Pat. No. 2,273,785. As an example: a solution of alkenones is treated with aqueous sodium hypochlorite (typically 12%=industrial bleach) and the mixture is stirred vigorously (generally 1-2 hours). The mixture is then made acidic (pH<5) by the addition of HCl. Stirring is stopped and the layers are allowed to separate. The organic phase containing the alkenoic acids is recovered, dried, and concentrated in vacuo.

Synthesis of Alkenone-Derived Anionic Surfactants

Alkenoic acids can be directly converted to their corresponding anionic carboxylate surfactants by deprotonation with an appropriate base (e.g., NaOH or KOH). Other alkenoic acid- or alkenol-derived anionic surfactants can generally proceed via a condensation or substitution reaction. For example, sulfate surfactants can be formed by reactions of alkenols with $SO_3$·pyridine. In a typical experiment, a solution of alkenols (10 g) in solvent (e.g., dimethylformamide/dichloromethane (DMF/DCM) mixtures) is treated with pyridine·$SO_3$ (Pyr·$SO_3$) (5 g) and the mixture is stirred at room temperature for 1-5 h (monitored by thin layer chromatography (TLC)). Solvent is then removed under reduced pressure to give the corresponding pyridinium alkenol sulfate salt. To exchange the pyridinium counterion with sodium, the product is treated with a sodium alcoholate solvent (e.g., sodium methoxide or sodium ethoxide (NaOMe or NaOEt)) at which point the sodium alkenol sulfate can precipitate out of solution. The suspension is then centrifuged and the supernatant removed. Referring to FIG. 8, the product compound B (usually a white powder) can be rinsed (e.g., with methanol) to remove traces of pyridine and dried at 40-50° C. under vacuum (typically $3\times10^{-2}$ mbar). Compound purity can be determined by NMR spectroscopy.

Other alkenone-derived sulfates can be synthesized by first condensing an alkenoic acid or alkenol with an appropriate linker (e.g., diol) prior to sulfation. As an example: alkenoic acids can be condensed with an excess of ethylene glycol (typically 3 molar equivalents) in the presence of acid (e.g., $H_2SO_4$, approximately 2 mol %) at room temperature for approximately 24 h. Neutralization (e.g., with $NaHCO_3$) followed by portioning with water and an organic solvent (e.g., dichloromethane) then allows for isolation of the alkenol ethylene glycol condensation product that can be sulfated according to the procedure above to yield compound A (FIG. 8).

Synthesis of Alkenone-Derived Betaine Surfactants

Alkenones can be converted to amino acids C by means of Strecker reaction (see, e.g., Strecker, A., "Ueber die kunstliche Bildung der Milchsäure and einen neuen, dem Glycocoll homologen Korper," *Annalen der Chemie and Pharmazie* 1850, 75, 27-45. (b) Strecker, A. (1854). "Ueber einen neuen aus Aldehyd—Ammoniak and Blausäure entstehenden Körper," Annalen der Chemie and Pharmazie 1854, 91, 349-351) or one of its many recent variants. See, e.g., Duthaler, R.O., *Tetrahedron* 1994, 50, 1539-1650 and Shibasaki, M.; Kanai, M.; Mita, K., *Org. React.* 2008, 70, 1. In a standard reaction, alkenones are treated with NaCN (1.0 equiv.) in the presence of $NH_4Cl$ (0.5 equiv.) and $MgSO_4$ (0.5 equiv.) in 7 M $NH_3$ in MeOH (3.0 equiv.) at 30° C. for 34. See, e.g., Kuethe, J.T.; Gauthier, D.R.; Beutner, G.L.; Yasuda, N., *J. Org. Chem.* 2007, 72, 7469-7472. Ammonia and methanol (MeOH) are then removed under reduced pressure. Dilution with solvent (e.g., diethyl ether, methyl t-butyl ether (MTBE), $CH_2Cl_2$) and removal of the inorganic solids by filtration then gives the corresponding amino nitrile that can be hydrolyzed under either aqueous basic or aqueous acidic conditions.

Betaine surfactants (e.g., D and E, FIG. 8) can be prepared by condensation of alkenols with an appropriate ammonium phosphonate or ammonium carbonate respectively. For the synthesis of D, alkenols are treated with 2-choloro-1,3,2-dioxaphospholane (1.3 equiv.) in the presence of trimethylamine (1.75 equiv.). See, e.g., Zhang, Q.; Horst, R.; Geralt, M.; Ma, X.; Hong, W-X.; Finn, M.G.; Stevens, R.C.; Wiitrich, K., *J. Am. Chem. Soc.* 2008, 130, 7357-7363. After 4 h at room temperature, triethylammonium chloride is removed by filtration and the mixture is concentrated under reduced pressure. The product is then redissolved in solvent (typically acetonitrile), to which is added trimethylamine and the mixture is heated to 70° C. for approximately 48 h. Concentration under vacuum then yields the betaine ammonium phosphonate D.

For the synthesis of E, alkenols are first treated with carbonyl diimidazole (1.1 equiv.) in the presence of ethanediamine (1.3 equiv.). See, e.g., Yoshida, K-I. et al., *Bioorg. Med. Chem.* 2007, 15, 7807-7097. The resulting carbamate is then N-alkylated with tert-butyl bromoacetate followed by acidic hydrolysis of the tent-butyl ester to give betaine E.

Synthesis of Alkenol Polyoxyethylene Surfactants

Ethoxylation of alkenols can be carried out by the reaction of alkenols with ethylene oxide under either basic or Lewis acid catalysis. In a typical reaction, to a solution of alkenols (1 mol) in solvent (tetrahydofuran (THF) or DCM) is added base (e.g., sodium hydride, 0.1 mol) followed by ethylene oxide (25 mol). The reaction is quenched with aqueous acid (e.g., 1M HCl) and the product obtained by precipitation from solvent. Similarly, sodium or potassium alkenolates can be made to react with poly(ethyleneglycol)methane sulfonates which can lower polydispersity. See, e.g., A.K. Khachadurian, C.H. Fung, T. van Es, F. Davis, *Biochim. Biophys. Acta* 1981, 665, 434.

Preparation of Alkenone-Derived Cationic Surfactants

Cationic ammonium alkenone derivatives can be made from alkenones via any number of reductive amination reactions. In a typical procedure, alkenones are dissolved in solvent (e.g., tetrahydrofuran, dichloromethane, or dichloroethane) to which is added an amine (e.g., dimethylamine (1.0-2.0 equiv.), a reducing agent (e.g., sodium cyanoborohydride (1.3-1.6 equiv.)) with or without acid (e.g., acetic acid (1.0-2.0 equiv.)). See, e.g., A.F. Abdel-Magid, K.G. Carson, B.D. Harris, C.A. Maryanoff, R.D. Shah, *J. Org. Chem.,* 1996, 61, 3849-3862. The mixture is stirred for 0.5-74 hours before quenching with aq. brine and extracting with ethyl acetate or dichloromethane. The organic extracts are dried over sodium sulfate, filtered, and concentrated in vacuo. The resulting alkenamine can then be dissolved in tetrahydrofuran and treated with an alkyl halide (e.g., iodomethane (1.0-2.0 equiv.) to generate the corresponding cationic ammonium compound.

Alternatively, the ammonium cation can be incorporated through an acyl linker (e.g., compound G, FIG. 8) in analogy to compound E.

Preparation of Alkenone Choline Phosphonate Encapsulating Agents

Glycerol alkenone-based liposomes, nanoemulsions, and lipid nanoparticles can be prepared beginning with monoacylated alkenoic acid derivatives (e.g., GMA). Condensation of GMA with choline phosphate (1.0 equiv.) in refluxing ethanol (~85° C.) would provide the monoalkenone monocholine phosphonate adduct.

Alternatively, alkenones can be coupled with choline alfoscerate. In a typical reaction, to a solution of alkenones (1.0 equiv.) and choline alfoscerate (2-4 equiv.) in $CH_2Cl_2$ was added dicyclohexycarbodiimide (DCC, 1.1 equiv.) followed by catalytic dimethylaminopyridine (DMAP, 3-10 mol %) and the mixture was stirred for 24-72 h. See, e.g., Neises, B.; Steglich, W., *Angew. Chem. Int. Ed.* 1978, 17, 522-524. The ratio of alkenones to choline alfoscerate can be manipulated to select for the formation of mono- or di-alkenone choline phosphates. Fatty acids can also be introduced in this manner with or without isolation of monoalkenone choline phosphate to produce alkenone/fatty acid choline phosphate hybrids.

PREPARATION OF COMPOSITIONS

Preparation of Alkenone-Based Abrasive Soaps

Treatment of algal oil with KOH or NaOH at 60° C. results in saponification of the acylglycerols as described in the '460 Application. The resulting mixture generally contains approximately 50% w/w soap, with the remainder being primarily alkenones (~15% w/w) and pigments such as chlorophylls. Pigments can be removed by decolorization with an adsorbent as described above, pre- or post-saponification to yield a light yellow-colored soap/alkenone mixture. Alternatively, isolated alkenones and soaps can be recombined to provide specific alkenone/soap compositions of varying concentrations (e.g., 10-50% w/w alkenones). Alkenone solubility in these mixtures is <1 mg/mL, so these compounds remain as waxy solids.

Preparation of Alkenone Cleansers

Compositions can be made by combining isolated (and decolorized) alkenones with surfactants to provide exfoliating skin care products.

Preparation of Alkenone-Containing Skin-Care Products

Compositions can be made directly made from the algal oil containing primarily acylglycerols (approximately 40%) along with alkenones (approximately 10%) and pigments like chlorophylls and carotenoids. Decolorization of this material using similar technology to that described for the alkenones would provide a yellow-colored composition with elevated triglyceride (50-60%) and alkenone (15-20%) contents. Compositions can also be prepared starting with isolated (and if desired decolorized) alkenones. Depending on their intended use (e.g., cream, ointment, paste, lotion, gel), other ingredients can include, for example, water, oils, hydrocarbons, alcohols, free fatty acids plus emulsifiers, thickening agents, and preservatives.

The following examples are provided to illustrate, not limit, the invention.

Example 1 describes extraction and purification of alkenones from microalgae. of the lipids. Example 2 describes the hydrogenation of alkenones to alkenones. Example 3 describes the reduction of alkenones to alkenols. Example 4 describes oxidation of alkenones to alkenoic acids. Example 5 describes the synthesis of alkenone-derived anionic surfactants. Example 6 describes the synthesis of alkenone-derived betaine surfactants. Example 7 describes the synthesis of alkenol polyoxyethylene surfactants. Example 8 describes the preparation of alkenone-derived cationic surfactants. Example 9 describes the preparation of alkenone choline phosphonate encapsulating agents.

EXAMPLES

Example 1. Microalgae and Extraction of Alkenones

Algae are processed and the lipids extracted according to methods described in the '460 Application. As a specific example, dry *Isochrysis* biomass is extracted by Soxhlet using hexanes as solvent to provide an algal oil containing approximately 50% w/w fatty acid derivatives (e.g., acylglycerols) and 15% w/w alkenones. An exemplary alkenone profile of this material is presented in Table 2. See, e.g., O'Neil, G.W.; Carmichael, C. A.; Goepfert, T.J.; Fulton, J.M.; Knothe, G.; Lau, C.P.L.; Lindell, S.R.; Mohammady, N. G-E.; Van Mooy, B.A.S.; Reddy, C.M., "Beyond Fatty Acid Methyl Esters: Expanding the Renewable Carbon Profile with Alkenones from *Isochrysis* sp." Energy Fuels 2012, 26, 2434-2441.

TABLE 2

| Typical alkenone composition of *Isochrysis* sp. | | |
|---|---|---|
| Alkenones | mg/g of *Isochrysis* sp. algal oil | mg/g of dry weight of *Isochrysis* sp. |
| Me 37:3 (8E, 15E, 22E) | 67 | 13 |
| Me 37:2 (15E, 22E) | 43 | 9 |
| Et 38:3 (9E, 16E, 23E) | 8 | 2 |
| Et 38:2 (9E, 16E, 23E) | 37 | 7 |
| Me 39:3 (8E, 15E, 22E) | 2 | 1 |
| Me 39:2 (15E, 22E) | 4 | 1 |
| Total Alkenones | 161 | 33 |

Separation of Neutral and Polar Lipids

Alkenones and other neutral lipids can be separated from polar lipids (e.g., fatty acids) contained in the algal oil by treatment with KOH or NaOH at 60° C. as described in the '460 Application. The resulting saponified acylglycerols (i.e. soaps) can be partitioned into water while neutral lipids are extracted with an organic solvent (typically hexanes). Mass balance is generally 40% neutral lipids.

Recovery of Free Fatty Acids

Reacidification of aqueous soap mixtures with HCl produces the corresponding free fatty acids. These can then be extracted with an organic solvent such as hexanes. Mass recoveries of free fatty acids is typically 60% w/w from the algal oil.

Isolation and Purification of Alkenones from the Neutral Lipids

Figure 1C:
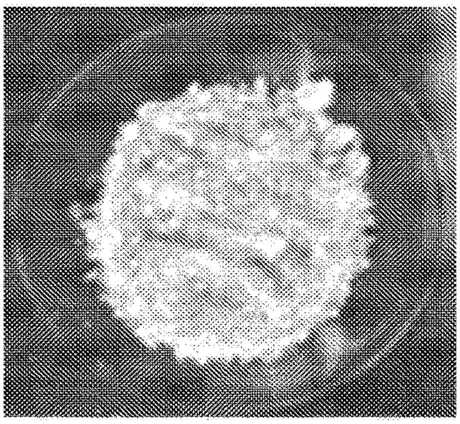
FIG. 1C is a photograph of alkenones extracted from algae, showing a white waxy solid.

Alkenones can be isolated and purified from the neutral lipids as described in the '460 Application by chromatography on silica and recrystallization (FIG. 1C). As shown in the "Materials and Methods" section of the '460 Application, the overall mass recovery for combined free fatty acids (FFAs) and neutral lipids from Isochrysis algal oil was 40% neutral lipids +60% FFAs. The neutral lipids (10 g) were processed to give pure alkenones (typically 4 g) as a white solid.

Decolorization of Alkenones

Brilliant white alkenones (i.e., purified alkenones 108 of FIG. 7) that can be preferred for certain applications can be obtained by decolorization using various solid materials such as clays or activated carbon based on technology used in vegetable oil refining. In a typical procedure, to the neutral lipids (10 g, pre- or post-silica chromatography) in hexanes (50 mL) at 60° C. was added the acidic clay montmorillonite K 10 (1 g) and the mixture was stirred for 3 h. The reaction was hot-filtered to remove the MK10, and upon cooling to room temperature alkenones (typically 4 g) crystallized out of solution. This procedure can be repeated as necessary to achieve the desired level of decolorization.

Example 2. Hydrogenation of Alkenones to Alkanones

To a solution of alkenones in ethyl acetate was added palladium on carbon (10% wt Pd, 10% w/w alkenones) and the mixture was placed under an atmosphere of hydrogen (1 atm.). The reaction was stirred for 6 h before removing the palladium by filtration through cotton and concentrating the solution in vacuo. The resulting alkanones were obtained as an off-white solid (98% yield, mp. =55-58° C.).

Example 3. Reduction of Alkenones to Alkenols

Figure 9:
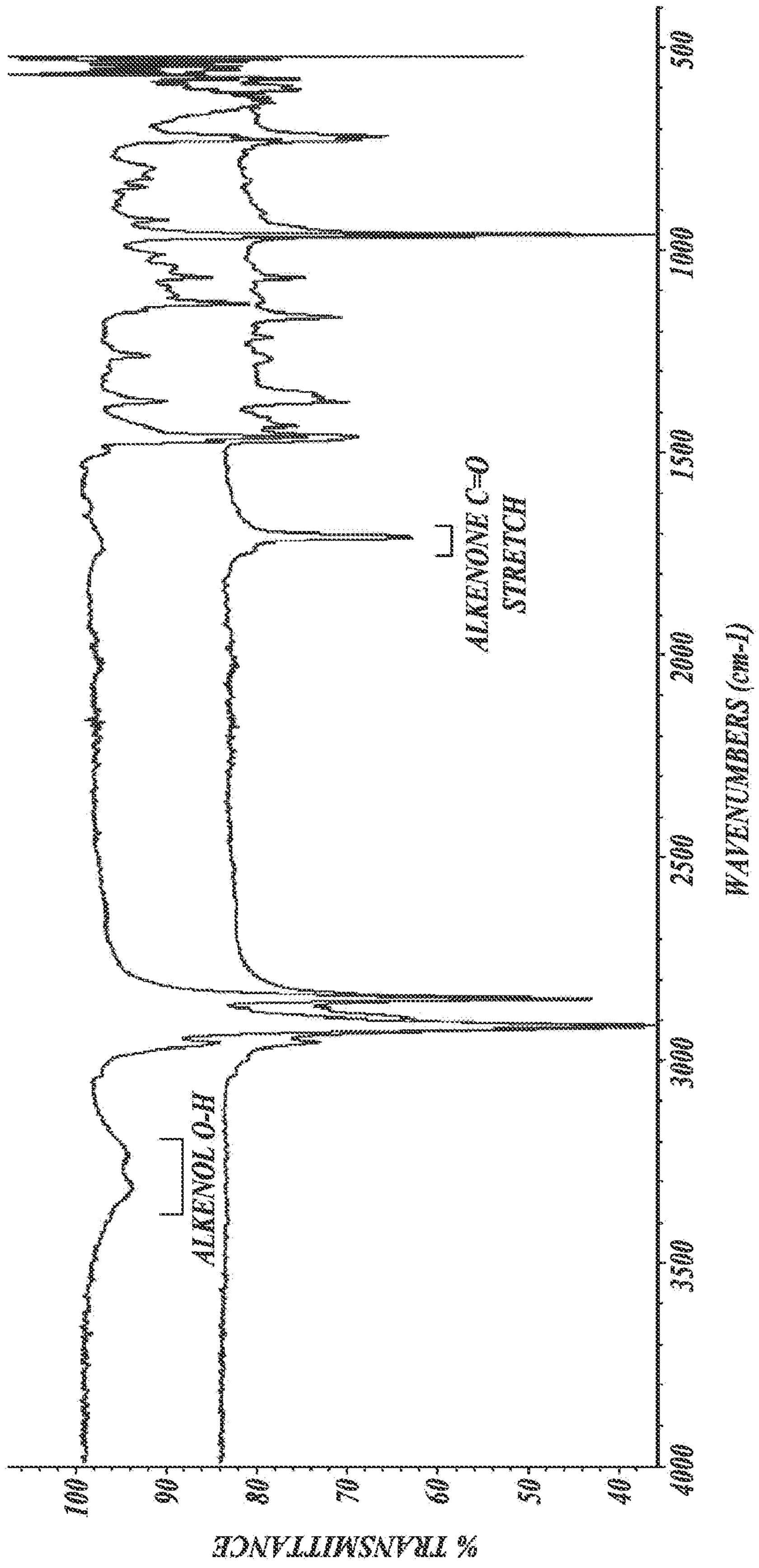
FIG. 9 shows exemplary IR spectra of alkenones and alkenols, where the loss of the C═O stretch at 1711 $cm^{-1}$ and emergence of a new O—H stretch occurs upon reduction of the alkenones to alkenols.

In a standard reaction, alkenones are dissolved in a mixture of an alcoholic solvent (ROH) and ethereal solvent (e.g., tetrahydrofuran) to which is added sodium borohydride ($NaBH_4$) and the mixture is stirred for 1 h. The reaction is then quenched with saturated aq. Brine, and extracted with an organic solvent (e.g., ethyl acetate, diethyl ether). The organic phase is concentrated in vacuo to yield the alkenol products that can be used without further purification (yields are generally>90%). Referring to FIG. 9, the reduction of alkenones to alkenols can be observed by the loss of the C═O stretch at about 1711 cm−1 and emergence of a new O—H stretch in an infrared spectrum

Example 4. Oxidation of Alkenones to Alkenoic Acids

A solution of alkenones is treated with aqueous sodium hypochlorite (typically 12%=industrial bleach) and the mixture is stirred vigorously (generally 1-2 hours). The mixture is then made acidic (pH<5) by the addition of HCl. Stirring is stopped and the layers are allowed to separate. The organic phase containing the alkenoic acids is recovered, dried, and concentrated in vacuo.

Example 5. Synthesis of Alkenone-Derived Anionic Surfactants

A solution of alkenols (10 g) in solvent (e.g., DMF/DCM mixtures) is treated with Pyr. $SO_3$ (5 g) and the mixture is stirred at room temperature for 1-5 h (monitored by TLC). Solvent is then removed under reduced pressure to give the corresponding pyridinium alkenol sulfate salt. To exchange the pyridinium counterion with sodium, the product is treated with a sodium alcoholate solvent (e.g., NaOMe or NaOEt) at which point the sodium alkenol sulfate can precipitate out of solution. The suspension is then centrifuged and the supernatant removed. The product compound B (FIG. 8, usually a white powder) can be rinsed (e.g., with methanol) to remove traces of pyridine and dried at 40-50° C. under vacuum (typically $3\times10^{-2}$ mbar). Compound purity can be determined by NMR spectroscopy.

Alkenone-derived anionic surfactants of structure A (FIG. 8) can be made by condensing alkenoic acids with an excess of ethylene glycol (typically 3 molar equivalents) in the presence of acid (e.g., H2504, approximately 2 mol %) at room temperature for approximately 24 h. Neutralization (e.g., with $NaHCO_3$) followed by portioning with water and an organic solvent (e.g., dichloromethane) then allows for isolation of the alkenol ethylene glycol condensation product that can be sulfated according to the procedure above to yield compound A.

Example 6. Synthesis of Alkenone-Derived Betaine Surfactants

Alkenones are treated with NaCN (1.0 equiv.) in the presence of $NH_4Cl$ (0.5 equiv.) and $MgSO_4$ (0.5 equiv.) in 7 M $NH_3$ in MeOH (3.0 equiv.) at 30° C. for 34. See, e.g., Kuethe, J.T.; Gauthier, D.R.; Beutner, G.L.; Yasuda, N., *J. Org. Chem.* 2007, 72, 7469-7472. Ammonia and MeOH are then removed under reduced pressure. Dilution with solvent (e.g., diethyl ether, MTBE, $CH_2Cl_2$) and removal of the inorganic solids by filtration then gives the corresponding amino nitrile that can be hydrolyzed under either aqueous basic or aqueous acidic conditions to provide C (FIG. 8).

Betaine surfactants (e.g., D and E, FIG. 8) can be prepared by condensation of alkenols with an appropriate ammonium phosphonate or ammonium carbonate respectively. For the synthesis of D, alkenols are treated with 2-choloro-1,3,2-dioxaphospholane (1.3 equiv.) in the presence of trimethylamine (1.75 equiv.). After 4 h at room temperature, triethylammonium chloride is removed by filtration and the mixture is concentrated under reduced pressure. The product is then redissolved in solvent (typically acetonitrile), to which is added trimethylamine and the mixture is heated to 70° C. for approximately 48 h. Concentration under vacuum then yields the betaine ammonium phosphonate D.

For the synthesis of E, alkenols are first treated with carbonyl diimidazole (1.1 equiv.) in the presence of ethanediamine (1.3 equiv.). The resulting carbamate is then N-alkylated with tent-butyl bromoacetate followed by acidic hydrolysis of the tert-butyl ester to give betaine E.

Example 7. Synthesis of Alkenol Polyoxyethylene Surfactants

To a solution of alkenols (1 mol) in solvent (THF or DCM) is added base (e.g., sodium hydride, 0.1 mol) followed by ethylene oxide (25 mol). The reaction is quenched with aqueous acid (e.g., 1M HCl) and the product obtained by precipitation from solvent. Similarly, sodium or potassium alkenolates can be made to react with poly(ethyleneglycol)methane sulfonates which can lower polydispersity.

Example 8. Preparation of Alkenone-Derived Cationic Surfactants

Alkenones are dissolved in solvent (e.g., tetrahydrofuran, dichloromethane, or dichloroethane) to which is added an amine (e.g., dimethylamine (1.0-2.0 equiv.), a reducing agent (e.g., sodium cyanoborohydride (1.3-1.6 equiv.)) with or without acid (e.g., acetic acid (1.0-2.0 equiv.)). The mixture is stirred for 0.5-74 hours before quenching with aq. brine and extracting with ethyl acetate or dichloromethane. The organic extracts are dried over sodium sulfate, filtered, and concentrated in vacuo. The resulting alkenamine can then be dissolved in tetrahydrofuran and treated with an alkyl halide (e.g., iodomethane (1.0-2.0 equiv.) to generate the corresponding cationic ammonium compound.

Alternatively, the ammonium cation can be incorporated through an acyl linker (e.g., compound G, FIG. 8) in analogy to compound E.

Example 9. Preparation of Alkenone Choline Phosphonate Encapsulating Agents

Glycerol alkenone-based liposomes, nanoemulsions, and lipid nanoparticles can be prepared beginning with monoacylated alkenoic acid derivatives (e.g., GMA). Condensation of GMA with choline phosphate (1.0 equiv.) in refluxing ethanol (~85° C.) would provide the monoalkenone monocholine phosphonate adduct.

Alternatively alkenones can be coupled with choline alfoscerate: to a solution of alkenones (1.0 equiv.) and choline alfoscerate (2-4 equiv.) in $CH_2Cl_2$ was added dicyclohexycarbodiimide (DCC, 1.1 equiv.) followed by catalytic dimethylaminopyridine (DMAP, 3-10 mol %) and the mixture was stirred for 24-72 h. The ratio of alkenones to choline alfoscerate can be manipulated to select for the formation of mono- or di-alkenone choline phosphates. Fatty acids can also be introduced in this manner with or without isolation of monoalkenone choline phosphate to produce alkenone/fatty acid choline phosphate hybrids.

The embodiments of the invention in which an exclusive property or privilege is claimed are defined as follows:

1. A personal care composition, comprising:

at least one compound of Formula (I):

(I)

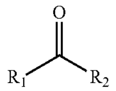

wherein

R1 is methyl or ethyl; and

R2 is a C30-45 alkenyl having at least one trans double carbon-carbon bond, or R2 is a C30-45 alkyl; provided that the compound of Formula (I) is not

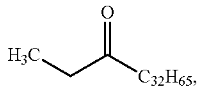,

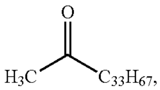,

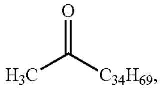,

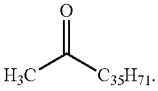.

2. The personal care composition of claim 1, wherein the personal care composition comprises greater than 70% by weight of compounds of Formula (I).

3. The personal care composition of claim 1, wherein the personal care composition comprises greater than 75% by weight of compounds of Formula (I).

4. The personal care composition of claim 1, wherein the personal care composition is white in color in reference to a total haptophyte microalgae extract.

5. The personal care composition of claim 4, wherein the personal care composition is brilliant white in color.

6. The personal care composition of claim 1, wherein the personal care composition has a melting point of between 55° C. and 70° C.

7. A method for non-therapeutic treatment of a human skin, the method comprising:

selecting the personal care composition of claim 1; and topically applying to skin in need thereof the personal care composition of claim 1.

* * * * *